US006992193B2

(12) United States Patent  
Le Bourdonnec et al.

(10) Patent No.: US 6,992,193 B2  
(45) Date of Patent: Jan. 31, 2006

(54) SULFONYLAMINO PHENYLACETAMIDE DERIVATIVES AND METHODS OF THEIR USE

(75) Inventors: Bertrand Le Bourdonnec, East Fallowfield, PA (US); Christopher William Ajello, Lansdale, PA (US); Roland E. Dolle, King of Prussia, PA (US)

(73) Assignee: Adolor Corporation, Exton, PA (US)

( * ) Notice: Subject to any disclaimer, the term of this patent is extended or adjusted under 35 U.S.C. 154(b) by 187 days.

(21) Appl. No.: 10/458,135

(22) Filed: Jun. 10, 2003

(65) Prior Publication Data

US 2004/0254156 A1 Dec. 16, 2004

(51) Int. Cl.  
*C07D 275/04* (2006.01)

(52) U.S. Cl. ..................................................... 548/207
(58) Field of Classification Search ................ 548/207; 544/269.7; 514/211.1  
See application file for complete search history.

(56) References Cited

U.S. PATENT DOCUMENTS

| | | | |
|---|---|---|---|
| 4,065,573 A | 12/1977 | Lednicer | 424/278 |
| 4,098,904 A | 7/1978 | Szmuszkovicz | 424/324 |
| 4,145,435 A | 3/1979 | Szmuszkovicz | 424/274 |
| 4,212,878 A | 7/1980 | Lednicer et al. | 424/274 |
| 4,359,476 A | 11/1982 | Kaplan et al. | 424/274 |
| 4,438,130 A | 3/1984 | Kaplan | 424/274 |
| 4,663,343 A | 5/1987 | Horwell et al. | 514/429 |
| 4,906,655 A | 3/1990 | Horwell et al. | 514/422 |
| 5,232,978 A | 8/1993 | Gottschlich et al. | 514/422 |
| 5,472,961 A | 12/1995 | Gottschlich et al. | 514/230.5 |
| 5,532,266 A | 7/1996 | Gottschlich et al. | 514/428 |
| 5,688,955 A | 11/1997 | Kruse et al. | 546/276.4 |
| 5,804,595 A | 9/1998 | Portoghese et al. | 514/428 |
| 6,057,323 A * | 5/2000 | Zhang et al. | 514/13 |
| 6,177,438 B1 | 1/2001 | Nagase et al. | 514/280 |

FOREIGN PATENT DOCUMENTS

| | | |
|---|---|---|
| EP | 0 483 580 A3 | 5/1992 |
| WO | WO 91/08206 | 6/1991 |

OTHER PUBLICATIONS

Jain, K.K., "A guide to drug evaluation for chronic pain," *Emerging Drugs*, 2000, 5(2), 241–257.  
Buschmann, H. (Eds.), et al., *Analgesics, Wiley–VCH, Verlag GMbH & Co. KgaA, Weinheim*, 2002.  
De Sousa, S.E., et al., "Two useful methods for the preparation of (R) and (S)–N–methyl–1–phenyl–2–(1–pyrrolidinyl)ethanamine," *Tetrahedron: Asymmetry*, 1997, 8(15), 2613–2618.  
Greene, T.W., et al., "Protective Groups in Organic Synthesis," 2nd Ed., Wiley & Sons, 1991.

Guidance for Industry: "In Vivo Drug Metabolism/Drug Interaction Studies—Study Design, Data Analysis and Recommendations for dosing and Labeling," *The Food and Drug Administration*, Nov. 1999.  
Iyengar, S., et al., "*Kappa* opiate agonists modulate the hypothalamic–pituitary–adrenocortical axis in the rat," *J. Pharmacol. Exp. Ther.*, 1986, 238(2), 429–436.  
Leander, J.D., et al., "Diuresis and suppression of vasopressin by *Kappa* opioids: comparison with *MU* and *Delta* opioids and clonidine," *J. Pharmacol. Exp. Ther.*, 1985, 234(2), 463–469.  
Lutz, R.A., et al., "Opioid receptors and their pharmacological profiles," *J. Receptor Res.*, 1992, 12(3), 267–286.  
Mansour, A., et al., "Anatomical distribution of opioid receptors in mammalians: an overview," *Handbook of Experimental Pharmacology*, 1993, vol. 104/I, 79–105.  
Manzanares, J., et al., "Kappa–opioid–receptor–mediated regulation to α–melanocyte–stimulating hormone secretion and tuberohypophysical dopaminergic neuronal activity," *Neuroendocrinology*, 1990, 52, 200–205.  
Morley, J.E., et al., "Involvement of dynorphin and the kappa opioid receptor in feeding," *Peptides*, 1983, 4, 797–800.  
Raynor, K., et al., "Pharmacological characterization of the cloned κ–δ–, and μ–opioid receptors," *Mol. Pharmacol.*, 1993, 45, 330–334.  
Remington's Pharmaceutical Sciences, *Mack Publishing Co., Easton, PA*, 1980.  
Simon, E.J., "Opioid receptors and Endogenous opioid peptides," *Med. Res. Rev.*, 1991, 11(4), 357–374.  
Wood, P.L., "Multiple opiate receptors: support for unique mu, delta and kappa sites," *Neuropharmacology*, 1982, 21, 487–497.

* cited by examiner

*Primary Examiner*—Joseph K. McKane  
*Assistant Examiner*—R. Waller  
(74) *Attorney, Agent, or Firm*—Woodcock Washburn LLP

(57) ABSTRACT

Sulfonylamino phenylacetamide derivatives of the general formula

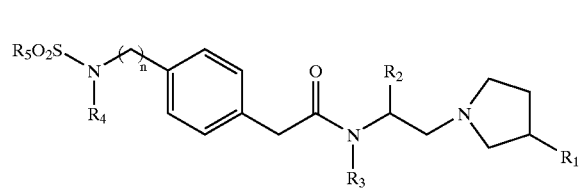

are disclosed. Pharmaceutical compositions containing the compounds and methods for their use are also disclosed. In certain embodiments, the compounds of the invention that, preferably:
(1) bind with high affinity to κ opioid receptors;
(2) display good opioid receptor selectivity of κ versus μ and κ versus δ; and
(3) do not substantially inhibit cytochrome P450 enzymatic activity, in particular CYP2D6, CYP2C9 and CYP3A4.

23 Claims, No Drawings

SULFONYLAMINO PHENYLACETAMIDE DERIVATIVES AND METHODS OF THEIR USE

FIELD OF THE INVENTION

The invention relates to sulfonylamino phenylacetamide derivatives, pharmaceutical compositions containing these compounds, and methods for their use. In certain embodiments, the sulfonylamino phenylacetamide derivatives are agonists of the κ opioid receptor and are useful, inter alia, for treating and/or preventing pain, pruritus, and gastrointestinal disorders.

BACKGROUND OF THE INVENTION

Opium and its derivatives are potent analgesics that also have other pharmacological effects, and exert their effects by interacting with high-affinity receptors. It has been shown by investigators that there are at least three major opioid receptor types in the central nervous system (hereinafter CNS) and in the periphery. These receptors, known as mu (μ), delta (δ) and kappa (κ), have distinct pharmacological profiles, anatomical distributions and functions. See, for example: Wood, P. L., *Neuropharmacology,* 21, 487–497, 1982; Simon, E. J., *Med. Res. Rev.,* 11, 357–374, 1991; Lutz et al., *J. Recept. Res.,* 12, 267–286, 1992; and Mansour et al., *Opioid I,* ed. Herz, A. (Springer, Berlin), 79–106, 1993. The δ receptors are abundant in CNS and mediate analgesia, gastrointestinal motility and various hormonal functions. The μ receptors bind morphine-like drugs and mediate the opiate phenomena associated with morphine, including analgesia, opiate dependence, cardiovascular and respiratory functions, and several neuroendocrine effects. The κ receptors have a wide distribution in CNS and mediate a spectrum of functions including the modulation of drinking, water balance, food intake, tussis, gut motility, temperature control and various endocrine functions. They also produce analgesia. See, for example: Leander et al., *J. Pharmacol. Exp. Ther.,* 234, 463–469, 1985; Morley et al., *Peptides* 4, 797–800, 1983; Manzanares et al., *Neuroendocrinology,* 52, 200–205, 1990; and Iyengar et al., *J. Pharmacol. Exp. Ther,* 238, 429–436, 1986; U.S. Pat. No. 6,177,438.

Most clinically used opioid analgesics, such as morphine and codeine, act as μ receptor agonists. These opioids have well-known, undesirable and potentially dangerous dependence-forming side effects. Compounds that are κ-receptor agonists act as analgesics through interaction with κ opioid receptors. The advantage of these agonists over the classical μ receptor agonists, such as morphine, lies in their ability to cause analgesia while being devoid of morphine-like behavioral effects and addiction liability.

A large number of classes of compounds which act as agonists at κ opioid receptors have been described in the art including the following illustrative classes of compounds:

U.S. Pat. No. 4,065,573 discloses 4-amino-4-phenylcyclohexane ketal compounds allegedly having analgesic activity.

U.S. Pat. No. 4,145,435 discloses N-(2-aminocycloaliphatic)-phenylacetamide compounds allegedly having analgesic activity and narcotic antagonist activity.

U.S. Pat. No. 4,098,904 discloses N-(2-aminocycloaliphatic)-benzoamides and naphthamides allegedly useful for relieving pain.

U.S. Pat. No. 4,212,878 discloses phenylacetamide derivatives allegedly having analgesic properties and reduced physical dependence liability properties, relative to morphine and methadone.

U.S. Pat. No. 4,359,476 discloses substituted cycloalkane-amides allegedly useful as analgesics and having low abuse liability.

U.S. Pat. No. 4,438,130 discloses 1-oxa-, aza- and thia-spirocyclic compounds allegedly having analgesic activity, low physical dependence and abuse liability properties and little dysphoric inducing properties.

U.S. Pat. No. 4,663,343 discloses substituted naphthalenyloxy-1,2-diaminocyclohexyl amides allegedly useful as analgesics.

U.S. Pat. No. 4,906,655 discloses 1,2-cyclohexylaminoaryl amides allegedly having high κ-opioid affinity, selectivity and potency and allegedly useful as analgesics, diuretics, anti-inflammatory and psychotherapeutic agents.

U.S. Pat. No. 5,532,266 discloses arylacetamides allegedly having high κ-opioid affinity useful as pharmaceutical agents for providing an analgesic effect and/or neuroprotective effect.

U.S. Pat. No. 5,688,955 discloses substituted piperidines, substituted naphthalenes, aryl-substituted amides, and cyclohexyl-substituted amides having κ opioid agonist activity, compositions containing them and methods of using them as analgesics.

U.S. Pat. No. 5,804,595 discloses amino acid conjugates of substituted 2-phenyl-N-[1-(phenyl)-2-(1-heterocycloalkyl- or heterocycloaryl-)ethyl]acetamides allegedly useful for selectively agonizing κ opioid receptors in mammalian tissue.

Although numerous compounds have been reported to be potent and selective κ opioid agonists, many of these compounds were found in our assays to be very potent inhibitors of a number of human cytochrome P450 enzymes, particularly CYP2D6, CYP2C9 and CYP3A4.

Cytochrome P450 enzymes are heme-containing membrane proteins localized in the smooth endoplasmic reticulum of numerous tissues, including, in particular, the liver. This family of enzymes catalyzes a wide variety of oxidative and reductive reactions and has activity towards a chemically diverse group of substrates. Oxidative biotransformations catalyzed by cytochrome P450 monooxygenases include aromatic and side chain hydroxylation, N-, O-, and S-dealkylation, N- and S-oxidation, N-hydroxylation, deamination, dehalogenation, and desulfuration. These enzymes are the major catalysts of drug biotransformation reactions and also serve an important detoxification role in the body. The cytochrome P450 enzymes catalyze oxidative reactions of toxins in the body by making them more water-soluble.

Because some of these κ agonist compounds are potent inhibitors of cytochrome P450 enzymes, they interfere with the body's ability to detoxify. For example, lethal clinical consequences can result from CYP3A4 inhibitors with drugs that are metabolized by this enzyme. As a further example, the use of an inhibitor of cytochrome P450 could render a normally safe and effective dose of a drug that is metabolized by cytochrome P450 toxic because the enzyme does not reduce the level of the drug in the patient to safe levels. In this way, the inhibition of cytochrome P450 enzymes could preclude clinical development of a given compound. For further discussion on drug interactions, see, for example, the *Guidance for Industry: In Vivo Drug Metabolism/Drug Interaction Studies—Study Design, Data Analysis, and Recommendations for Dosing and Labeling* prepared by the Food and Drug Administration (November 1999), the disclosure of which is incorporated herein by reference.

Thus, there is still an unfulfilled need for compounds with κ opioid receptor activity that may be used in methods to provide beneficial pharmaceutical characteristics while minimizing undesirable side effects generally associated with administering these exogenous opioids, particularly inhibition of cytochrome P450 enzymes. The present invention is directed to these, as well as other important ends.

SUMMARY OF THE INVENTION

The present invention is generally directed to sulfonylamino phenylacetamide derivatives, pharmaceutical compositions containing these compounds, and methods for their pharmaceutical use. The present invention relates to compounds that, preferably:

(1) bind with high affinity to κ opioid receptors;
(2) display good opioid receptor selectivity of κ versus μ and κ versus δ; and
(3) do not substantially inhibit cytochrome P450 enzymatic activity, in particular CYP2D6, CYP2C9 and CYP3A4.

In one embodiment, the invention is directed to compounds of Formula I:

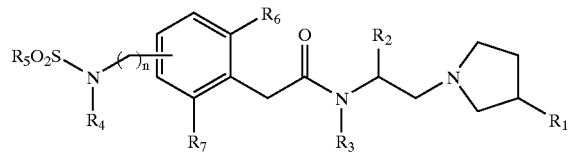

I or a stereoisomer, prodrug, pharmaceutically acceptable salt, hydrate, solvate, acid salt hydrate, N-oxide or isomorphic crystalline form thereof;

wherein, independently:

n is an integer from 0 to 4, preferably 1;

$R_1$ is H or —OH;

$R_2$ is alkyl, preferably isopropyl, or aryl, preferably phenyl;

$R_3$ is H, alkyl, preferably methyl, or, when taken together with $R_2$, forms a 4- to 7-membered heterocycloalkyl ring;

$R_4$ is H or alkyl;

$R_5$ is alkyl, aryl or heteroaryl; and $R_6$ and $R_7$ are H.

In certain preferred embodiments, $R_1$ is H. In other preferred embodiments, $R_1$ is —OH. In certain preferred embodiments, $R_2$ is alkyl, with isopropyl being more preferred. In yet other preferred embodiments, $R_2$ is aryl, with phenyl being more preferred. In preferred embodiments, $R_3$ is H or alkyl, and more preferably, $R_3$ is methyl. In certain preferred embodiments, $R_2$ and $R_3$ form a 4- to 7-membered heterocycloalkyl ring.

In certain preferred embodiments of the present invention, the compounds of Formula I have the structure corresponding to Formula II:

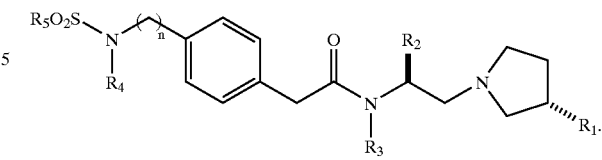

II

In certain preferred embodiments of the present invention, the compounds of Formula I have the structure corresponding to Formula III:

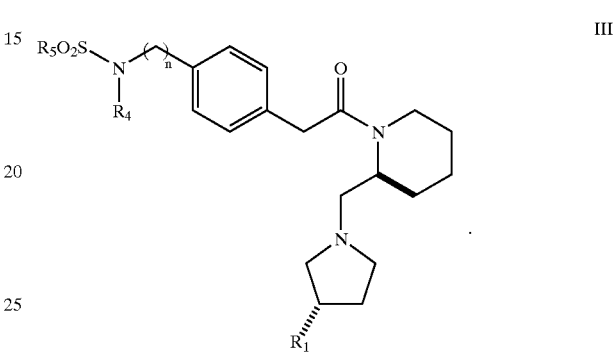

III

In a second embodiment, the invention is directed to pharmaceutical compositions, comprising:
a pharmaceutically acceptable carrier; and
an effective amount of a compound of Formula I.

In preferred embodiments, the pharmaceutical compositions may further comprise an effective amount of at least one opioid. Suitable opioids include, for example, alfentanil, buprenorphine, butorphanol, codeine, dezocine, dihydrocodeine, fentanyl, hydrocodone, hydromorphone, levorphanol, meperidine (pethidine), methadone, morphine, nalbuphine, oxycodone, oxymorphone, pentazocine, propiram, propoxyphene, sufentanil, tramadol and mixtures thereof.

In another embodiment, the invention is directed to pharmaceutical compositions comprising a pharmaceutically acceptable carrier and an effective amount of a compound of Formula I. In certain preferred embodiments, the pharmaceutical compositions may further comprise an opioid and/or another active ingredient selected from the group consisting of antibiotics, antivirals, antifungals, anti-inflammatories, anesthetics and mixtures thereof.

In another embodiment, the invention is directed to methods of binding opioid receptors, including κ opioid receptors, in a patient in need thereof, comprising the step of administering to the patient an effective amount of a compound of Formula I.

In yet another embodiment, the invention is directed to methods for preventing or treating gastrointestinal dysfunction comprising the step of administering to a patient in need thereof, a composition comprising an effective amount of a compound of Formula I.

In other embodiments, the invention is directed to methods for preventing or treating ileus comprising the step of administering to a patient in need thereof, a composition comprising an effective amount of a compound of Formula I.

In another embodiment, the invention is directed to methods for preventing or treating pain comprising the step of administering to a patient in need thereof, a composition comprising an effective amount of an opioid and an effective amount of a compound of Formula I.

In another embodiment, the invention is directed to methods for preventing or treating pruritic dermatoses and conditions characterized by pruritic dermatosis as a symptom, including allergic dermatitis, atopy, contact dermatitis, psoriasis, eczema, opioid-induced pruritus, and insect bites, comprising the step of administering to a patient in need thereof, a composition comprising an effective amount of a compound of Formula I.

In another embodiment, the invention is directed to methods for preventing or treating cerebral edema, comprising the step of administering to a patient in need thereof, a composition comprising an effective amount of a compound of Formula I.

In other embodiments, the invention is directed to methods for preventing or treating oxygen supply deficiency of the central nervous system, comprising the step of administering to a patient in need thereof, a composition comprising an effective amount of a compound of Formula I.

In another embodiment, the invention is directed to methods for inducing diuresis, comprising the step of administering to a patient in need thereof, a composition comprising an effective amount of a compound of Formula I.

In yet another embodiment, the invention is directed to methods for preventing or treating tussis, comprising the step of administering to a patient in need thereof, a composition comprising an effective amount of a compound of Formula I.

DETAILED DESCRIPTION OF ILLUSTRATIVE EMBODIMENTS

As employed above and throughout the disclosure, the following terms, unless otherwise indicated, shall be understood to have the following meanings.

As used herein, "alkyl" refers to an optionally substituted, saturated straight, branched, or cyclic hydrocarbon having from about 1 to about 20 carbon atoms (and all combinations and subcombinations of ranges and specific numbers of carbon atoms therein), with from about 1 to about 8 carbon atoms, herein referred to as "lower alkyl", being preferred. Alkyl groups include, but are not limited to, methyl, ethyl, n-propyl, isopropyl, n-butyl, isobutyl, t-butyl, n-pentyl, cyclopentyl, isopentyl, neopentyl, n-hexyl, isohexyl, cyclohexyl, cyclooctyl, adamantyl, 3-methylpentyl, 2,2-dimethylbutyl, and 2,3-dimethylbutyl.

As used herein, "alkenyl" refers to an alkyl group of at least 2 carbon atoms having one or more double bonds, wherein alkyl is as previously defined. Alkenyl groups can be optionally substituted.

As used herein, "alkynyl" refers to an alkyl group of at least 2 carbon atoms having one or more triple bonds, wherein alkyl is as previously defined. Alkynyl groups can be optionally substituted.

As used herein, "aryl" refers to an optionally substituted, mono-, di-, tri-, or other multicyclic aromatic ring system having from about 5 to about 50 carbon atoms (and all combinations and subcombinations of ranges and specific numbers of carbon atoms therein), with from about 6 to about 10 carbons being preferred. Non-limiting examples include, for example, phenyl, naphthyl, anthracenyl, and phenanthrenyl.

As used herein, "perhaloalkyl" refers to an alkyl group, wherein all of the hydrogens are replaced by halo (F, Cl, Br, I) atoms, and alkyl is as previously defined.

As used herein, "aralkyl" refers to alkyl radicals bearing an aryl substituent and having from about 6 to about 50 carbon atoms (and all combinations and subcombinations of ranges and specific numbers of carbon atoms therein), with from about 6 to about 10 carbon atoms being preferred. Aralkyl groups can be optionally substituted. Non-limiting examples include, for example, benzyl, diphenylmethyl, triphenylmethyl, phenylethyl, and diphenylethyl.

As used herein, "heteroaryl" refers to an optionally substituted, mono-, di-, tri-, or other multicyclic aromatic ring system that includes at least one, and preferably from 1 to about 4 sulfur, oxygen, or nitrogen heteroatom ring members. Heteroaryl groups can have, for example, from about 3 to about 50 carbon atoms (and all combinations and subcombinations of ranges and specific numbers of carbon atoms therein), with from about 4 to about 10 carbons being preferred. Non-limiting examples of heteroaryl groups include, for example, pyrryl, furyl, pyridyl, 1,2,4-thiadiazolyl, pyrimidyl, thienyl, isothiazolyl, imidazolyl, tetrazolyl, pyrazinyl, pyrimidyl, quinolyl, isoquinolyl, thiophenyl, benzothienyl, isobenzofuryl, pyrazolyl, indolyl, purinyl, carbazolyl, benzimidazolyl, and isoxazolyl.

As used herein, "cycloalkyl" refers to an optionally substituted, alkyl group having one or more rings in their structures and having from about 3 to about 20 carbon atoms (and all combinations and subcombinations of ranges and specific numbers of carbon atoms therein), with from about 3 to about 10 carbon atoms being preferred. Multi-ring structures may be bridged or fused ring structures. Groups include, but are not limited to, cyclopropyl, cyclobutyl, cyclopentyl, cyclohexyl, cyclooctyl, and adamantyl.

As used herein, "alkylcycloalkyl" refers to an optionally substituted ring system comprising a cycloalkyl group having one or more alkyl substituents. Exemplary alkylcycloalkyl groups include 2-methylcyclohexyl, 3,3-dimethylcyclopentyl, trans-2,3-dimethylcyclooctyl, and 4-methyldecahydronaphthalenyl.

As used herein, "heteroaralkyl" refers to an optionally substituted, heteroaryl substituted alkyl radicals having from about 2 to about 50 carbon atoms (and all combinations and subcombinations of ranges and specific numbers of carbon atoms therein), with from about 6 to about 25 carbon atoms being preferred. Non-limiting examples include 2-(1H-pyrrol-3-yl)ethyl, 3-pyridylmethyl, 5-(2H-tetrazolyl)methyl, and 3-(pyrimidin-2-yl)-2-methylcyclopentanyl.

As used herein, "heterocycloalkyl" refers to an optionally substituted, mono-, di-, tri-, or other multicyclic aliphatic ring system that includes at least one, and preferably from 1 to about 4 sulfur, oxygen, or nitrogen heteroatom ring members. Heterocycloalkyl groups can have from about 3 to about 20 carbon atoms (and all combinations and subcombinations of ranges and specific numbers of carbon atoms therein), with from about 4 to about 10 carbons being preferred. The heterocycloalkyl group may be unsaturated, and may also be fused to aromatic rings. Examples of heterocycloalkyl groups include, for example, tetrahydrofuranyl, tetrahydrothienyl, piperidinyl, pyrrolidinyl, isoxazolidinyl, isothiazolidinyl, pyrazolidinyl, oxazolidinyl, thiazolidinyl, piperazinyl, morpholinyl, piperadinyl, decahydroquinolyl, octahydrochromenyl, octahydro-cyclopenta[c]pyranyl, 1,2,3,4,-tetrahydroquinolyl, octahydro-[2]pyridinyl, decahydro-cycloocta[c]furanyl, and imidazolidinyl.

As used herein, the term "spiroalkyl" refers to an optionally substituted, alkylene diradical, both ends of which are bonded to the same carbon atom of the parent group to form a spirocyclic group. The spiroalkyl group, taken together with its parent group, as herein defined, has 3 to 20 ring atoms. Preferably, it has 3 to 10 ring atoms. Non-limiting examples of a spiroalkyl group taken together with its parent group include 1-(1-methyl-cyclopropyl)-propan-2-one, 2-(1-phenoxy-cyclopropyl)-ethylamine, and 1-methyl-spiro [4.7]dodecane.

As used herein, "alkoxy" and "alkoxyl" refer to an optionally substituted alkyl-O— group wherein alkyl is as previously defined. Exemplary alkoxy and alkoxyl groups include methoxy, ethoxy, n-propoxy, i-propoxy, n-butoxy, and heptoxy.

As used herein, "aryloxy" and "aryloxyl" refer to an optionally substituted aryl-O— group wherein aryl is as previously defined. Exemplary aryloxy and aryloxyl groups include phenoxy and naphthoxy.

As used herein, "aralkoxy" and "aralkoxyl" refer to an optionally substituted aralkyl-O— group wherein aralkyl is as previously defined. Exemplary aralkoxy and aralkoxyl groups include benzyloxy, 1-phenylethoxy, 2-phenylethoxy, and 3-naphthylheptoxy.

Typically, substitutions of chemical moieties include one or more substituents that replace hydrogen. Exemplary substituents include, for example, halo (e.g., F, Cl, Br, I), alkyl, cycloalkyl, alkylcycloalkyl, alkenyl, alkynyl, aralkyl, aryl, heteroaryl, heteroaralkyl, spiroalkyl, heterocycloalkyl, hydroxyl (—OH), alkoxyl, aryloxyl, aralkoxyl, nitro (—NO$_2$), cyano (—CN), amino (—NH$_2$), —N-substituted amino (—NHR"), —N,N-disubstituted amino (—N(R")R"), carboxyl (—COOH), —C(=O)R", —OR", —C(=O)OR", —NHC(=O)R", aminocarbonyl (—C(=O)NH$_2$), —N-substituted aminocarbonyl (—C(=O)NHR"), —N,N-disubstituted aminocarbonyl (—C(=O)N(R")R"), thiol, thiolato (SR"), sulfonic acid (SO$_3$H), phosphonic acid (PO$_3$H), S(=O)$_2$R", S(=O)$_2$NH$_2$, S(=O)$_2$NHR", S(=O)$_2$NR"R", NHS(=O)$_2$R", NR"S(=O)$_2$R", CF$_3$, CF$_2$CF$_3$, NHC(=O) NHR", NHC(=O)NR"R", NR"C(=O)NHR", NR"C(=O) NR"R", NR"C(=O)R" and the like. In relation to the aforementioned substituents, each moiety R" can be, independently, any of H, alkyl, cycloalkyl, alkenyl, aryl, aralkyl, heteroaryl, or heterocycloalkyl, for example.

As used herein, "opioid" refers to all agonist and antagonists with morphine-like activity as well as to naturally occurring and synthetic opioid peptides. Non-limiting examples of compounds with morphine-like activity include the family of drugs derived from opium, such as for example, morphine and codeine, thebaine, and a wide variety of semi synthetic related compounds derived therefrom.

As used herein, "analgesic" refers to pharmaceutical compounds that have the ability to reduce or eliminate pain and/or the perception of pain without a loss of consciousness.

As used herein, "effective amount" refers to an amount of a compound as described herein that may be therapeutically effective to inhibit, prevent or treat the symptoms of particular disease, disorder, condition, or side effect. Such diseases, disorders, conditions, and side effects include, but are not limited to, those pathological conditions associated with the administration of opioids (for example, in connection with the treatment and/or prevention of pain), wherein the treatment or prevention comprises, for example, inhibiting the activity thereof by contacting cells, tissues or receptors with compounds of the present invention. Thus, for example, the term "effective amount," when used in connection with opioids, or opioid replacements, for example, for the treatment of pain, refers to the treatment and/or prevention of the painful condition. The term "effective amount," when used in connection with anti-pruritic compounds, refers to the treatment and/or prevention of symptoms, diseases, disorders, and conditions typically associated with pruritus and other related dermatoses. The term "effective amount," when used in connection with compounds active against gastrointestinal dysfunction, refers to the treatment and/or prevention of symptoms, diseases, disorders, and conditions typically associated with gastrointestinal dysfunction. The term "effective amount," when used in connection with anti-ileus compounds, refers to the treatment and/or prevention of symptoms, diseases, disorders, and conditions typically associated with ileus. The term "effective amount", when used in connection with compounds useful in the treatment and/or prevention of cerebral edema, refers to the treatment and/or prevention of symptoms, diseases, disorders, and conditions typically associated with cerebral edema and other related conditions. The term "effective amount," when used in connection with anti-hypoxia compounds, refers to the treatment and/or prevention of symptoms, diseases, disorders, and conditions typically associated with hypoxia, such as oxygen supply deficiency to the central nervous system. The term "effective amount," when used in connection with anti-tussive compounds, refers to the treatment and/or prevention of tussis. The term "effective amount," when used in connection with diuretic compounds, refers to the inducement of diuresis.

As used herein, "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

As used herein, "in combination with," "combination therapy" and "combination products" refer, in certain embodiments, to the concurrent administration to a patient of opioids and the compounds of Formula I. When administered in combination, each component may be administered at the same time or sequentially in any order at different points in time. Thus, each component may be administered separately but sufficiently closely in time so as to provide the desired therapeutic effect.

As used herein, "dosage unit" refers to physically discrete units suited as unitary dosages for the particular individual to be treated. Each unit may contain a predetermined quantity of active compound(s) calculated to produce the desired therapeutic effect(s) in association with the required pharmaceutical carrier. The specification for the dosage unit forms of the invention may be dictated by (a) the unique characteristics of the active compound(s) and the particular therapeutic effect(s) to be achieved, and (b) the limitations inherent in the art of compounding such active compound(s).

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. These physiologically acceptable salts are prepared by methods known in the art, e.g., by dissolving the free amine bases with an excess of the acid in aqueous alcohol, or neutralizing a free carboxylic acid with an alkali metal base such as a hydroxide, or with an amine.

Compounds described herein throughout, can be used, or prepared in alternate forms. For example, many amino-containing compounds can be used or prepared as an acid addition salt. Often such salts improve isolation and handling properties of the compound. For example, depending on the reagents, reaction conditions and the like, compounds as described herein can be used or prepared, for example, as their hydrochloride or tessellate salts. Isomorphic crystalline forms, all chiral and racemic forms, N-oxide, hydrates, solvates, and acid salt hydrates, are also contemplated to be within the scope of the present invention.

Certain acidic or basic compounds of the present invention may exist as zwitterions. All forms of the compounds, including free acid, free base and zwitterions, are contemplated to be within the scope of the present invention. It is well known in the art that compounds containing both amino and carboxyl groups often exist in equilibrium with their zwitterionic forms. Thus, any of the compounds described herein throughout that contain, for example, both amino and carboxyl groups, also include reference to their corresponding zwitterions.

As used herein, "patient" refers to animals, including mammals, preferably humans.

As used herein, "stereoisomers" refers to compounds that have identical chemical constitution, but differ as regards the arrangement of the atoms or groups in space.

As used herein, "N-oxide" refers to compounds wherein the basic nitrogen atom of either a heteroaromatic ring or tertiary amine is oxidized to give a quaternary nitrogen bearing a positive formal charge and an attached oxygen atom bearing a negative formal charge.

As used herein, "gastrointestinal dysfunction" refers collectively to maladies of the stomach, small and large intestine. Non-limiting examples of gastrointestinal dysfunction include, for example, irritable bowel syndrome, opioid-bowel dysfunction, post-operative ileus, opioid-induced ileus, colitis, post-operative emesis, opioid-induced emesis, decreased gastric motility, decreased gastric emptying, inhibition of small intestinal propulsion, inhibition of large intestinal propulsion, increased amplitude of non-propulsive segmental contractions, constriction of sphincter of Oddi, increased anal sphincter tone, impaired reflex relaxation with rectal distention, diminished gastric, biliary, pancreatic or intestinal secretions, increased absorption of water from bowel contents, gastro-esophageal reflux, gastroparesis, cramping, bloating, abdominal or epigastric pain and discomfort, constipation, or delayed absorption of orally administered medications or nutritive substances.

As used herein, "pain" refers to the perception or condition of unpleasant sensory or emotional experience, associated with actual or potential tissue damage or described in terms of such damage. "Pain" includes, but is not limited to, two broad categories of pain: acute and chronic pain (Buschmann, H.; Christoph, T; Friderichs, E.; Maul, C.; Sundermann, B; eds.; *Analgesics*, Wiley-VCH, Verlag GMbH & Co. KgaA, Weinheim; 2002; Jain, K. K. "A Guide to Drug Evaluation For Chronic Pain"; *Emerging Drugs*, 5(2), 241–257(2000)). Non-limiting examples of pain include nociceptive pain, inflammatory pain, visceral pain, somatic pain, neuropathic pain, AIDS pain, cancer pain, phantom pain, and psychogenic pain, and pain resulting from hyperalgesia, allodynia and the like.

As used herein, "pruritus" refers to a symptom of a disease, disorder, or condition which is manifested by itching, that is, an uncomfortable sensation due to irritation of a peripheral sensory nerve.

As used herein, "tussis" refers to a coughing condition, and "antitussive" agents refer to those materials that modulate the coughing response.

As used herein, "diuretic" refers to an agent that modulates the water balance in a patient.

As used herein, "pruritic dermatosis" refers to any skin diseases, disorders, or conditions of which itching is a symptom. Non-limiting examples include allergic dermatitis, atopy, contact dermatitis, psoriasis, eczema, opioid-induced pruritus, uremic pruritus, and insect bites.

When any variable occurs more than one time in any constituent or in any formula, its definition in each occurrence is independent of its definition at every other occurrence. Combinations of substituents and/or variables are permissible only if such combinations result in stable compounds.

It is believed the chemical formulas and names used herein correctly and accurately reflect the underlying chemical compounds. However, the nature and value of the present invention does not depend upon the theoretical correctness of these formulae, in whole or in part. Thus it is understood that the formulas used herein, as well as the chemical names attributed to the correspondingly indicated compounds, are not intended to limit the invention in any way, including restricting it to any specific tautomeric form or to any specific optical; or geometric isomer, except where such stereochemistry is clearly defined.

In any of the above teachings, a compound of the invention may be either a compound of one of the formulae herein described, or a stereoisomer, prodrug, pharmaceutically acceptable salt, hydrate, solvate, acid salt hydrate, N-oxide or isomorphic crystalline form thereof.

The compounds employed in the methods of the present invention may exist in prodrug form. As used herein, "prodrug" is intended to include any covalently bonded carriers which release the active parent drug, for example, as according to Formula I or other formulas or compounds employed in the methods of the present invention in vivo when such prodrug is administered to a mammalian subject. Since prodrugs are known to enhance numerous desirable qualities of pharmaceuticals (e.g., solubility, bioavailability, manufacturing, etc.) the compounds employed in the present methods may, if desired, be delivered in prodrug form. Thus, the present invention contemplates methods of delivering prodrugs. Prodrugs of the compounds employed in the present invention, for example Formula I, may be prepared by modifying functional groups present in the compound in such a way that the modifications are cleaved, either in routine manipulation or in vivo, to the parent compound.

Accordingly, prodrugs include, for example, compounds described herein in which a hydroxy, amino, or carboxy group is bonded to any group that, when the prodrug is administered to a mammalian subject, cleaves to form a free hydroxyl, free amino, or carboxylic acid, respectively. Examples include, but are not limited to, acetate, formate and benzoate derivatives of alcohol and amine functional groups; and alkyl, carbocyclic, aryl, and alkylaryl esters such as methyl, ethyl, propyl, iso-propyl, butyl, isobutyl, sec-butyl, tert-butyl, cyclopropyl, phenyl, benzyl, and phenethyl esters, and the like.

In certain preferred embodiments, the compounds of the invention do not substantially inhibit cytochrome P450 enzymatic activity. As used herein, the phrase "do not substantially inhibit" means that the activity of the cytochrome P450 is reduced by less than about 25% of its normal physiological activity, preferably less than about 10%, more preferably less than about 5%, even more preferably less than about 1%. Preferably, this lack of effect on inhibition may be measured, as described in the examples, by measuring the inhibition of the cytochrome P450 catalyzed conversion of 7-methoxy-4-(aminomethyl)coumarin (MAMC) to 7-hydroxy-4-(aminomethyl)coumarin (HAMC) for CYP2D6 or the conversion of dibenzylfluorescein (DBF) to fluorescein for CYP2C9 and CYP3A4. In certain preferred embodiments, the compounds exhibit an $IC_{50}$ (CYP) greater than about 1,000 nM and, more preferably, greater than about 10,000 nM, particularly with respect to CYP2D6, CYP2C9 and/or CYP3A4, and most particularly with respect to CYP2D6.

In certain preferred embodiments, the compounds, pharmaceutical compositions and methods of the present invention may involve a peripheral opioid antagonist compound. In preferred form, the peripheral opioid antagonist compounds employed in the methods of the present invention exhibit high levels of activity with respect to peripheral tissue, such as, gastrointestinal tissue, while exhibiting reduced, and preferably substantially no, CNS activity. The term "peripheral" designates that the compound acts primarily on physiological systems and components external to the central nervous system. The phrase "substantially no CNS activity," as used herein, means that less than about 20% of the pharmacological activity of the compounds employed in the present methods is exhibited in the CNS, preferably less than about 15%, more preferably less than about 10%, even more preferably less than about 5% and most preferably 0% of the pharmacological activity of the compounds employed in the present methods is exhibited in the CNS.

Furthermore, it is preferred in certain embodiments of the invention that the compound does not substantially cross the blood-brain barrier and thereby decrease the beneficial activity of the opioid. The phrase "does not substantially cross," as used herein, means that less than about 20% by weight of the compound employed in the present methods crosses the blood-brain barrier, preferably less than about 15% by weight, more preferably less than about 10% by weight, even more preferably less than about 5% by weight and most preferably 0% by weight of the compound crosses the blood-brain barrier. Selected compounds can be evaluated for CNS penetration by determining plasma and brain levels following i.v. administration.

The compounds employed in the methods of the present invention may be prepared in a number of ways well known to those skilled in the art. The compounds can be synthesized, for example, by the methods described below, or variations thereon as appreciated by the skilled artisan. All processes disclosed in association with the present invention are contemplated to be practiced on any scale, including milligram, gram, multigram, kilogram, multikilogram or commercial industrial scale.

Compounds employed in the present methods may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare and isolate such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

As will be readily understood, functional groups present may contain protecting groups during the course of synthesis. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Preferred protecting groups include the benzyloxycarbonyl group and the tert-butyloxycarbonyl group. Other preferred protecting groups that may be employed in accordance with the present invention may be described in Greene, T. W. and Wuts, P. G. M., *Protective Groups in Organic Synthesis* 2d. Ed., Wiley & Sons, 1991.

The compounds employed in the methods of the present invention may be administered by any means that results in the contact of the active agent with the agent's site of action in the body of a patient. The compounds may be administered by any conventional means available for use in conjunction with pharmaceuticals, either as individual therapeutic agents or in a combination of therapeutic agents. For example, they may be administered as the sole active agent in a pharmaceutical composition, or they can be used in combination with other therapeutically active ingredients including, for example, opioid analgesic agents. In such combinations, selected compounds of the invention may provide equivalent or even enhanced therapeutic activity such as, for example, pain amelioration, while providing reduced adverse side effects associated with opioids, such as addiction or pruritus, by lowering the amount of opioid required to achieve a therapeutic effect.

The compounds are preferably combined with a pharmaceutical carrier selected on the basis of the chosen route of administration and standard pharmaceutical practice as described, for example, in *Remington's Pharmaceutical Sciences* (Mack Publishing Co., Easton, Pa., 1980), the disclosures of which are hereby incorporated herein by reference, in their entirety.

In addition to the pharmaceutical carrier, the compounds of Formula I may be co-administered with at least one opioid. Suitable opioids include alfentanil, buprenorphine, butorphanol, codeine, dezocine, dihydrocodeine, fentanyl, hydrocodone, hydromorphone, levorphanol, meperidine (pethidine), methadone, morphine, nalbuphine, oxycodone, oxymorphone, pentazocine, propiram, propoxyphene, sufentanil, tramadol and mixtures thereof.

Compounds of the present invention can be administered to a mammalian host in a variety of forms adapted to the chosen route of administration, e.g., orally or parenterally. Parenteral administration in this respect includes administration by the following routes: intravenous, intramuscular, subcutaneous, rectal, intraocular, intrasynovial, transepithelial including transdermal, ophthalmic, sublingual, and buccal; topically including ophthalmic, dermal, ocular, rectal, and nasal inhalation via insufflation aerosol.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparations should preferably contain at least 0.1% of active compound. The percentage of the compositions and preparations may, of course, be varied and may conveniently be, for example, from about 2 to about 6% of the weight of the unit. The amount of active compound in such therapeutically useful compositions is preferably such that a suitable dosage will be obtained. Preferred compositions or preparations according to the present invention may be prepared so that an oral dosage unit form contains from about 0.1 to about 1000 mg of active compound.

The tablets, troches, pills, capsules and the like may also contain one or more of the following: a binder, such as gum tragacanth, acacia, corn starch or gelatin; an excipient, such as dicalcium phosphate; a disintegrating agent, such as corn starch, potato starch, alginic acid and the like; a lubricant, such as magnesium stearate; a sweetening agent such as sucrose, lactose or saccharin; or a flavoring agent, such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. A syrup or elixir may contain the active compound, sucrose as a sweetening agent, methyl and propylparabens as preservatives, a dye and flavoring, such as cherry or orange flavor. Of course, any material used in preparing any dosage unit form is preferably pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or a pharmacologically acceptable salt can be prepared in water suitably mixed with a surfactant, such as hydroxypropylcellulose. A dispersion can also be prepared in glycerol, liquid polyethylene glycols, and mixtures thereof and in oils. Under ordinary conditions of storage and use, these preparations may contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. In all cases, the form is preferably sterile and fluid to provide easy syringability. It is preferably stable under the conditions of manufacture and storage and is preferably preserved against the contaminating action of microorganisms such as bacteria and fungi. The carrier may be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating, such as lecithin, by the maintenance of the required particle size in the case of a dispersion, and by the use of surfactants. The prevention of the action of microorganisms may be achieved by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions may be achieved by the use of agents delaying absorption, for example, aluminum monostearate, and gelatin.

Sterile injectable solutions may be prepared by incorporating the active compound in the required amount, in the appropriate solvent, with various of the other ingredients enumerated above, as required, followed by filtered sterilization. Generally, dispersions may be prepared by incorporating the sterilized active ingredient into a sterile vehicle that contains the basic dispersion medium and the required other ingredients from those enumerated above. In the case of sterile powders for the preparation of sterile injectable solutions, the preferred methods of preparation may include vacuum drying and the freeze drying technique that yield a powder of the active ingredient, plus any additional desired ingredient from the previously sterile-filtered solution thereof.

The therapeutic compounds of this invention may be administered to a patient alone or in combination with a pharmaceutically acceptable carrier. As noted above, the relative proportions of active ingredient and carrier may be determined, for example, by the solubility and chemical nature of the compound, chosen route of administration and standard pharmaceutical practice.

The dosage of the compounds of the present invention that will be most suitable for prophylaxis or treatment will vary with the form of administration, the particular compound chosen and the physiological characteristics of the particular patient under treatment. Generally, small dosages may be used initially and, if necessary, increased by small increments until the desired effect under the circumstances is reached. The therapeutic human dosage, based on physiological studies using rats, may generally range from about 0.01 mg to about 100 mg/kg of body weight per day, and all combinations and subcombinations of ranges therein. Alternatively, the therapeutic human dosage may be from about 0.4 mg to about 10 g or higher, and may be administered in several different dosage units from once to several times a day. Generally speaking, oral administration may require higher dosages.

The compounds of the invention may also be formulated with other optional active ingredients, in addition to the optional opioids, and in addition to the optional pharmaceutical-acceptable carriers. Other active ingredients include, but are not limited to, antibiotics, antivirals, antifungals, anti-inflammatories, including steroidal and non-steroidal anti-inflammatories, anesthetics, and mixtures thereof. Such additional ingredients include any of the following:

a. Antibacterial Agents

Aminoglycosides, such as Amikacin, Apramycin, Arbekacin, Bambennycins, Butirosin, Dibekacin, Dihydrostreptomycin, Fortimicin(s), Fradiomycin, Gentamicin, Ispamicin, Kanamycin, Micronomicin, Neomycin, Neomycin Undecylenate, Netilmicin, Paromomycin, Ribostamycin, Sisomicin, Spectinomycin, Streptomycin, Streptonicozid and Tobramycin;

Amphenicols, such as Azidamfenicol, Chloramphenicol, Chloramphenicol Palmirate, Chloramphenicol Pantothenate, Florfenicol, Thiamphenicol;

Ansamycins, such as Rifamide, Rifampin, Rifamycin and Rifaximin;

β-Lactams;

Carbapenems, such as Imipenem;

Cephalosporins, such as 1-Carba (dethia) Cephalosporin, Cefactor, Cefadroxil, Cefamandole, Cefatrizine, Cefazedone, Cefazolin, Cefixime, Cefinenoxime, Cefodizime, Cefonicid, Cefoperazone, Ceforanide, Cefotaxime, Cefotiam, Cefpimizole, Cefpirimide, Cefpodoxime Proxetil, Cefroxadine, Cefsulodin, Ceftazidime, Cefteram, Ceftezole, Ceftibuten, Ceftizoxime, Ceftriaxone, Cefuroxime, Cefuzonam, Cephacetrile Sodium, Cephalexin, Cephaloglycin, Cephaloridine, Cephalosporin, Cephalothin, Cephapirin Sodium, Cephradine and Pivcefalexin;

Cephamycins such as Cefbuperazone, Cefmetazole, Cefminox, Cefotetan and Cefoxitin;

Monobactams such as Aztreonam, Carumonam and Tigemonan;

Oxacephems such as Flomoxef and Moxolactam;

Penicillins such as Amidinocillin, Amdinocillin, Pivoxil, Amoxicillin, Ampicillan, Apalcillin, Aspoxicillin, Azidocillan, Azlocillan, Bacampicillin, Benzylpenicillinic Acid, Benzylpenicillin, Carbenicillin, Carfecillin, Carindacillin, Clometocillin, Cloxacillin, Cyclacillin, Dicloxacillin, Diphenicillin, Epicillin, Fenbenicillin, Floxicillin, Hetacillin, Lenampicillin, Metampicillin, Methicillin, Mezlocillin, Nafcillin, Oxacillin, Penamecillin, Penethamate Hydriodide, Penicillin G Benethamine, Penicillin G Benzathine, Penicillin G Benzhydrylamine, Penicillin G Calcium, Penicillin G Hydragamine, Penicillin G Potassium, Penicillin G. Procaine, Penicillin N, Penicillin O, Penicillin V, Penicillin V Benzathine, Penicillin V Hydrabamine, Penimepicycline, Phenethicillin, Piperacillin, Pivapicillin, Propicillin, Quinacillin, Sulbenicillin, Talampicillin, Temocillin and Ticarcillin;

Lincosumides such as Clindamycin and Lincomycin;

Macrolides such as Azithromycin, Carbomycin, Clarithromycin, Erythromycin(s) and Derivatives, Josamycin, Leucomycins, Midecamycins, Miokamycin, Oleandomycin, Primycin, Rokitamycin, Rosaramicin, Roxithromycin, Spiramycin and Troleandomycin;

Polypeptides such as Amphomycin, Bacitracin, Capreomycin, Colistin, Enduracidin, Enviomycin, Fusafungine, Gramicidin(s), Gramicidin S, Mikamycin, Polymyxin, Polymyxin β-Methanesulfonic Acid, Pristinamycin, Ristocetin, Teicoplanin, Thiostrepton, Tuberactinomycin, Tyrocidine, Tyrothricin, Vancomycin, Viomycin(s), Virginiamycin and Zinc Bacitracin;

Tetracyclines such as Spicycline, Chlortetracycline, Clomocycline, Demeclocycline, Doxycycline, Guamecycline, Lymecycline, Meclocycline, Methacycline, Minocycline, Oxytetracycline, Penimepicycline, Pipacycline, Rolitetracycline, Sancycline, Senociclin and Tetracycline; and others such as Cycloserine, Mupirocin, Tuberin.

b. Synthetic Antibacterials 2,4-Diaminopymmidines such as Brodimoprim, Tetroxoprim and Trimethoprim;

Nitrofurans such as Furaltadone, Furazolium, Nifuradene, Nifuratel, Nifurfoline, Nifurpirinol, Nifurprazine, Nifurtoinol and Nitrofurantoin;

Quinolones and analogs thereof, such as Amifloxacin, Cinoxacin, Ciprofloxacin, Difloxacin, Enoxacin, Fleroxacin, Flumequine, Lomefloxacin, Miloxacin, Nalidixic Acid, Norfloxacin, Ofloxacin, Oxolinic Acid, Perfloxacin, Pipemidic Acid, Piromidic Acid, Rosoxacin, Temafloxacin and Tosufloxacin;

Sulfonamides such as Acetyl Sulfamethoxypyrazine, Acetyl Sulfisoxazole, Azosulfamide, Benzylsulfamide, Chloramine-.beta., Chloramine-T, Dichloramine-T, Formosulfathiazole, $N^2$-Formyl-sulfisomidine, $N^4$-β-D-Glucosylsulfanilamide, Mafenide, 4'-(Methyl-sulfamoyl) sulfanilanilide, p-Nitrosulfathiazole, Noprylsulfamide, Phthalylsulfacetamide, Phthalylsulfathiazole, Salazosulfadimidine, Succinylsulfathiazole, Sulfabenzamide, Sulfacetamide, Sulfachlorpyridazine, Sulfachrysoidine, Sulfacytine, Sulfadiazine, Sulfadicramide, Sulfadimethoxine, Sulfadoxine, Sulfaethidole, Sulfaguanidine, Sulfaguanol, Sulfalene, Sulfaloxic Acid, Sulfamerazine, Sulfameter, Sulfamethazine, Sulfamethizole, Sulfamethomidine, Sulfamethoxazole, Sulfamethoxypyridazine, Sulfametrole, sulfamidochrysoidine, Sulfamoxole, Sulfanilamide, Sulfanilamidomethanesulfonic Acid Triethanolamine Salt, 4-Sulfanilamidosalicyclic Acid, $N^4$-Sulfanilylsulfanilamide, Sulfanilylurea, N-Sulfanilyl-3,4-xylamide, Sulfanitran, Sulfaperine, Sulfaphenazole, Sulfaproxyline, Sulfapyrazine, Sulfapyridine, Sulfasomizole, Sulfasymazine, Sulfathiazole, Sulfathiourea, Sulfatolamide, Sulfisomidine and Sulfisoxazole;

Sulfones, such as Acedapsone, Acediasulfone, Acetosulfone, Dapsone, Diathymosulfone, Glucosulfone, Solasulfone, Succisulfone, Sulfanilic Acid, p-Sulfanilylbenzylamine, p,p'-sulfonyldianiline-N,N'-digalactoside, Sulfoxone and Thiazolsulfone;

Others such as Clofoctol, Hexedine, Magainins, Methenamine, Methenamine Anhydromethylene-citrate, Methenamine Hippurate, Methenamine Mandelate, Methenamine Sulfosalicylate, Nitroxoline, Squalamine and Xibomol.

c. Antifungal (Antibiotics)

Polyenes such as Amphotericin-B, Candicidin, Dermostatin, Filipin, Fungichromin, Hachimycin, Hamycin, Lucensomycin, Mepartricin, Natamycin, Nystatin, Pecilocin, Perimycin; and others, such as Azaserine, Griseofulvin, Oligomycins, PyrroInitrin, Siccanin, Tubercidin and Viridin.

d. Antifungal (Synthetic)

Allylamines such as Naftifine and terbinafine;

Imidazoles such as Bifonazole, Butoconazole, Chlordantoin, Chlormidazole, Cloconazole, Clotrimazole, Econazole, Enilconazole, Finticonazole, Isoconazole, Ketoconazole, Miconazole, Omoconazole, Oxiconazole Nitrate, Sulconazole and Tioconazole;

Triazoles such as Fluconazole, Itraconazole, Terconazole;

Others such as Acrisorcin, Amorolfine, Biphenamine, Bromosalicylchloranilide, Buclosamide, Chlophenesin, Ciclopirox, Cloxyquin, Coparaffinate, Diamthazole, Dihydrochloride, Exalamide, Flucytosine, Halethazole, Hexetidine, Loflucarban, Nifuratel, Potassium Iodide, Propionic Acid, Pyrithione, Salicylanilide, Sulbentine, Tenonitrozole, Tolciclate, Tolindate, Tolnaftate, Tricetin, Ujothion, and Undecylenic Acid.

e. Antiglaucoma Agents

Antiglaucoma agents, such as Dapiprazoke, Dichlorphenamide, Dipivefrin and Pilocarpine.

f. Anti-inflammatory Agents

Corticosteroids, aminoarylcarboxylic Acid Derivatives such as Etofenamate, Meclofenamic Acid, Mefanamic Acid, Niflumic Acid;

Arylacetic Acid Derivatives such as Acemetacin, Amfenac Cinmetacin, Clopirac, Diclofenac, Fenclofenac, Fenclorac, Fenclozic Acid, Fentiazac, Glucametacin, Isozepac, Lonazolac, Metiazinic Acid, Oxametacine, Proglumetacin, Sulindac, Tiaramide and Tolmetin;

Arylbutyric Acid Derivatives such as Butibufen and Fenbufen;

Arylcarboxylic Acids such as Clidanac, Ketorolac and Tinoridine;

Arylpropionic Acid Derivatives such as Bucloxic Acid, Carprofen, Fenoprofen, Flunoxaprofen, Ibuprofen, Ibuproxam, Oxaprozin, Piketoprofen, Pirprofen, Pranoprofen, Protizinic Acid and Tiaprofenic Add;

Pyrazoles such as Mepirizole;

Pyrazolones such as Clofezone, Feprazone, Mofebutazone, Oxyphenbutazone, Phenylbutazone, Phenyl Pyrazolidininones, Suxibuzone and Thiazolinobutazone;

Salicylic Acid Derivatives such as Bromosaligenin, Fendosal, Glycol Salicylate, Mesalamine, 1-Naphthyl Salicylate, Olsalazine and Sulfasalazine;

Thiazinecarboxamides such as Droxicam, Isoxicam and Piroxicam; and others such as e-Acetamidocaproic Acid, S-Adenosylmethionine, 3-Amino-4-hydroxybutyric Acid, Amixetrine, Bendazac, Bucolome, Carbazones, Difenpiramide, Ditazol, Guaiazulene, Heterocyclic Aminoalkyl Esters of Mycophenolic Acid and Derivatives, Nabumetone, Nimesulide, Orgotein, Oxaceprol, Oxazole Derivatives, Paranyline, Pifoxime, 2-substituted-4,6-ditertiary-butyl-s-hydroxy-1,3-pyrimidines, Proquazone and Tenidap.

g. Antiseptics

Guanidines such as Alexidine, Ambazone, Chlorhexidine and Picloxydine;

Halogens/Halogen Compounds such as Bomyl Chloride, Calcium Iodate, Iodine, Iodine Monochloride, Iodine Trichloride, Iodoform, Povidone-Iodine, Sodium Hypochlorite, Sodium Iodate, Symclosene, Thymol Iodide, Triclocarban, Triclosan and Troclosene Potassium;

Nitrofurans such as Furazolidone, 2-(Methoxymethyl)-5-Nitrofuran, Nidroxyzone, Nifuroxime, Nifurzide and Nitrofurazone;

Phenols such as Acetomeroctol, Chloroxylenol, Hexachlorophene, 1-Naphthyl Salicylate, 2,4,6-Tribromo-m-cresol and 3',4',5-Trichlorosalicylanilide;

Quinolines such as Aminoquinuride, Chloroxine, Chlorquinaldol, Cloxyquin, Ethylhydrocupreine, Halquinol, Hydrastine, 8-Hydroxyquinoline and Sulfate; and others, such as Boric Acid, Chloroazodin, m-Cresyl Acetate, Cupric sulfate and Ichthammol.

h. Antivirals

Purines/Pyrimidinones, such as 2-Acetyl-Pyridine 5-((2-pyridylamino)thiocarbonyl) Thiocarbonohydrazone, Acyclovir, Dideoxyadenosine, dideoxycytidine, Dideoxyinosine, Edoxudine, Floxuridine, Ganciclovir, Idoxuridine, MADU, Pyridinone, Trifluridine, Vidrarbine and Zidovudline; and others such as Acetylleucine Monoethanolamine, Acridinamine, Alkylisooxazoles, Amantadine, Amidinomycin, Cuminaldehyde Thiosemicarbzone, Foscamet Sodium, Kethoxal, Lysozyme, Methisazone, Moroxydine, Podophyllotoxin, Ribavirin, Rimantadine, Stallimycin, Statolon, Thymosins, Tromantadine and Xenazoic Acid.

In yet another embodiment, the invention is directed to methods for preventing or treating gastrointestinal dysfunction comprising the step of administering to a patient in need thereof, a composition comprising an effective amount of a compound of Formula I.

In other embodiments, the invention is directed to methods for preventing or treating ileus comprising the step of administering to a patient in need thereof, a composition comprising an effective amount of a compound of Formula I.

In another embodiment, the invention is directed to methods for preventing or treating pain comprising the step of administering to a patient in need thereof, a composition comprising an effective amount of an opioid and an effective amount of a compound of Formula I.

In another embodiment, the invention is directed to methods for preventing or treating pruritic dermatoses and conditions characterized by pruritic dermatosis as a symptom, including allergic dermatitis, atopy, contact dermatitis, psoriasis, eczema, opioid-induced pruritus, and insect bites, comprising the step of administering to a patient in need thereof, a composition comprising an effective amount of a compound of Formula I.

In another embodiment, the invention is directed to methods for preventing or treating cerebral edema, comprising the step of administering to a patient in need thereof, a composition comprising an effective amount of a compound of Formula I.

In other embodiments, the invention is directed to methods for preventing or treating oxygen supply deficiency of the central nervous system, comprising the step of administering to a patient in need thereof, a composition comprising an effective amount of a compound of Formula I.

In another embodiment, the invention is directed to methods for inducing diuresis, comprising the step of administering to a patient in need thereof, a composition comprising an effective amount of a compound of Formula I.

In yet another embodiment, the invention is directed to methods for preventing or treating tussis, comprising the step of administering to a patient in need thereof, a composition comprising an effective amount of a compound of Formula I.

The sulfonylamino phenylacetamide derivatives of the present invention may be prepared according to the general method depicted in Schemes 1–7.

The synthesis of the acetamides 9a-c and the methylsulfonamides 10a-c is outlined in Scheme 1. Treatment of the bromophenylacetic acids 1a-c with methanol in the presence of sulfuric acid provided the methyl esters 2a-c which reacted with copper (I) cyanide to give the nitrites 3a-c. Catalytic hydrogenation of 3a-c using Pd/C as catalyst provided the primary amines 4a-c which were further protected as their tert-butyloxycarbonyl (Boc) derivatives by treatment with tert-butyloxycarbonylanhydride. Hydrolysis of the resulting carbamates 5a-e using lithium hydroxide gave the carboxylic acids 6a-c which were coupled to the diamine A (De Sousa, S. E.; O'Brien, P.; Poumellec, P.; Tetrahedron:Asymmetry, 1997, 8, 2613–2618) under standard peptide coupling procedure to provide the amides 7a-c. Removal of the Boc protecting group under acidic conditions provided the primary amines 8a-c which reacted with acetyl chloride or methylsulfonyl chloride to give the acetamides 9a-c and sulfonamides 10a-c respectively.

The sulfonamides 13a-k may be prepared according to the Scheme 2. Condensation of the primary amine 4c with various sulfonyl chloride derivatives afforded the sulfonamides 11a-k which were converted to the corresponding carboxylic acids 12a-k under basic conditions. Coupling of the acids 12a-k with the diamine B (Bathe, A.; Helfert, B.; Aackerman, K-A.; Gottschlich, R.; Stein, I.; Budak, J. DE 19,827,633, 1999) using TBTU as peptide coupling agent provided the sulfonamides 13a-k.

The synthesis of the N-methylsulfonamide 19 is outlined in Scheme 3. Treatment of the carboxylic acid 14 with methanol in the presence of EDC provided the methyl ester 15 which reacted with methylamine to give the secondary amine 16. Condensation of 16 with mesyl chloride gave the sulfonamide 17, which was hydrolyzed to the carboxylic acid derivative 18 under basic conditions. Coupling of 18 with the diamine B using TBTU as peptide coupling agent provided the target compound 19.

Condensation of the commercially available aniline (Aldrich Chemical Company) derivative 20 with mesyl chloride (Scheme 4) provided the sulfonamide 21, which was hydrolyzed to the carboxylic acid 22 using lithium hydroxide. Coupling of 22 with the diamine B afforded the methylsulfonamide 23.

Condensation of 15 with potassium cyanide gave the nitrile 24, which was converted to the primary amine 25 by hydrogenation using Pd/C as catalyst (Scheme 5). Treatment of 25 with mesyl chloride provided the sulfonamide 26, which was hydrolyzed under basic conditions to give the carboxylic acid 27. Coupling of 27 with the diamine B provided the desired target compound 28.

The sulfonamide 35 may prepared in 7 steps from the methyl ester 15 (Scheme 6). Treatment of 15 with calcium carbonate in a dioxane/water mixture provided the primary alcohol 29, which was oxidized to the aldehyde 30 using the Dess-Martin Periodinane as oxidizing agent. Horner-Emmons type condensation of the aldehyde 30 with (triphenylphosphoranylidene)acetonitrile provided the acrylonitrile derivative 31 which was converted to the primary amine 32 by hydrogenation in the presence of palladium hydroxide (Pearlman's catalyst). Treatment of 32 with mesyl chloride provided the sulfonamide 33, which was hydrolyzed under basic conditions to give the carboxylic acid 34. Coupling of 34 with the diamine B provided the desired target compound 35.

Condensation of the carboxylic acid derivative 12a with the diamines C (EP-A-0,670,318) or D (WO 91/08206) using TBTU as peptide coupling agent gave the amides 36a and 36b, as shown in Scheme 7a and Scheme 7b, respectively.

Scheme 1:

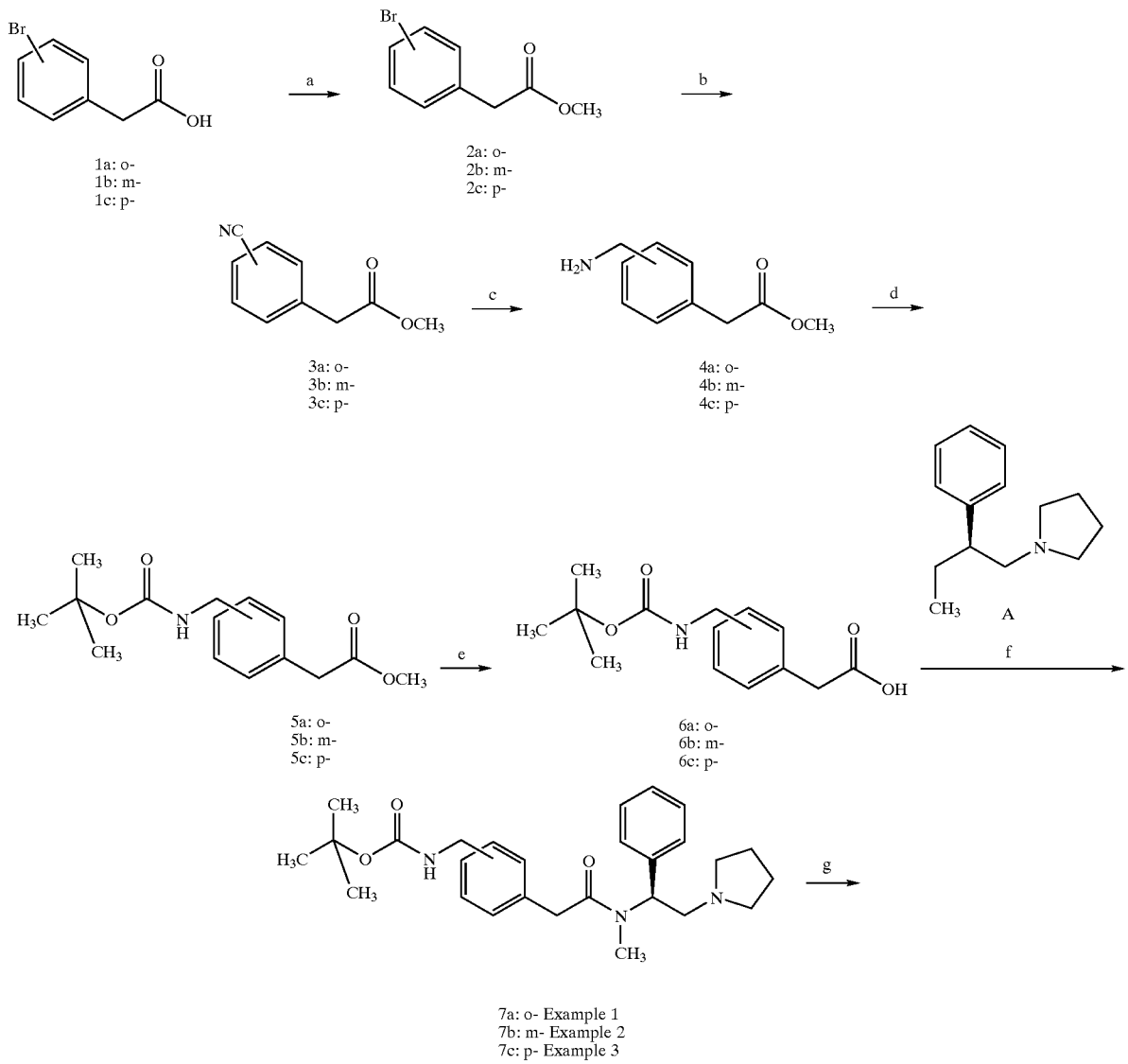

7a: o- Example 1
7b: m- Example 2
7c: p- Example 3

21

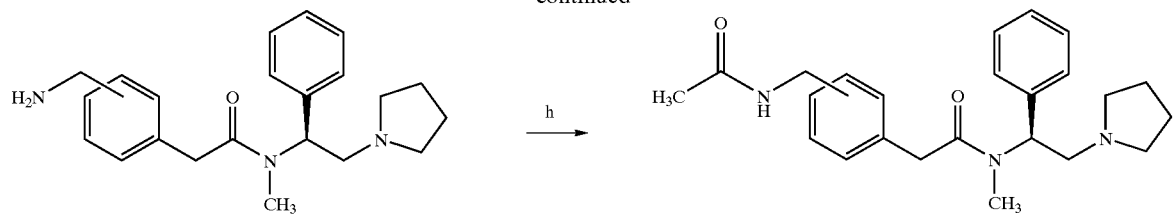

8a: o- Example 4
8b: m- Example 5
8c: p- Example 6

22

-continued

9a: o- Example 7
9b: m- Example 8
9c: p- Example 9

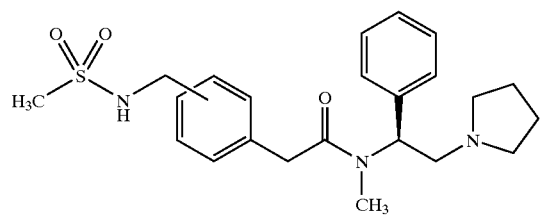

10a: o- Example 10
10b: m- Example 11
10c: p- Example 12

Reagents and Condition:
a) $H_2SO_4$, $CH_3OH$; b) CuCN, DMF; c) $H_2$, Pd/C, HCl, $CH_3OH$;
d) $BOC_2O$, $Et_3N$, $CH_2Cl_2$; e) LiOH, $H_2O$, THF; f) A, TBTU, $iPr_2EtN$, $CH_3CN$; g) HCl, $Et_2O$, $CH_3OH$; h) $CH_3COCl$, $Et_3N$, $CH_2Cl_2$;
i) $CH_3SO_2Cl$, $Et_3N$, $CH_2Cl_2$.

Scheme 2:

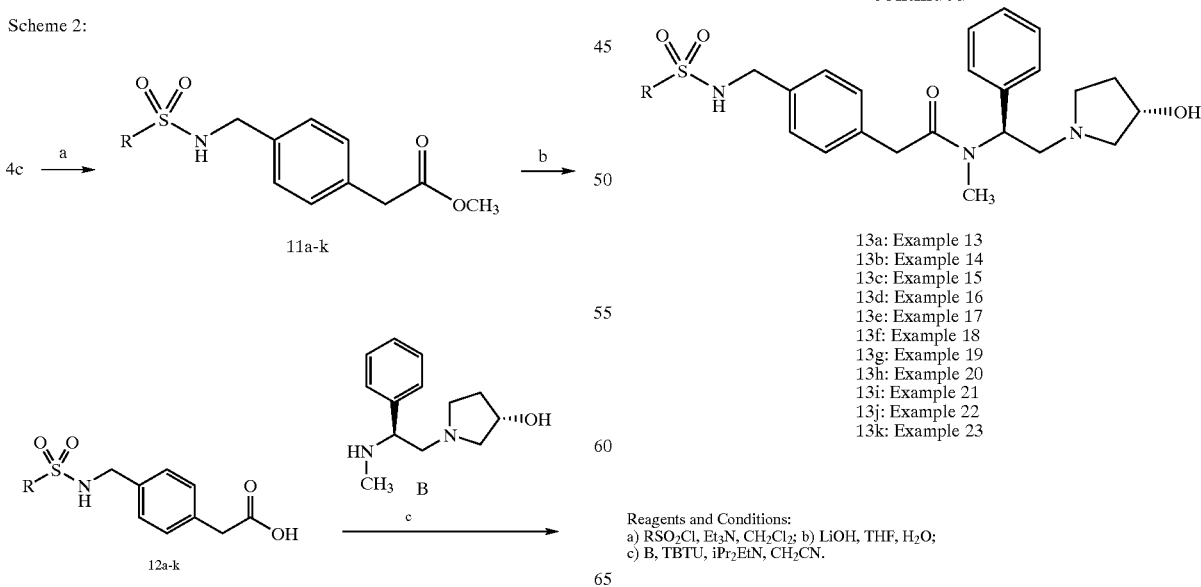

13a: Example 13
13b: Example 14
13c: Example 15
13d: Example 16
13e: Example 17
13f: Example 18
13g: Example 19
13h: Example 20
13i: Example 21
13j: Example 22
13k: Example 23

Reagents and Conditions:
a) $RSO_2Cl$, $Et_3N$, $CH_2Cl_2$; b) LiOH, THF, $H_2O$;
c) B, TBTU, $iPr_2EtN$, $CH_2CN$.

Scheme 3:
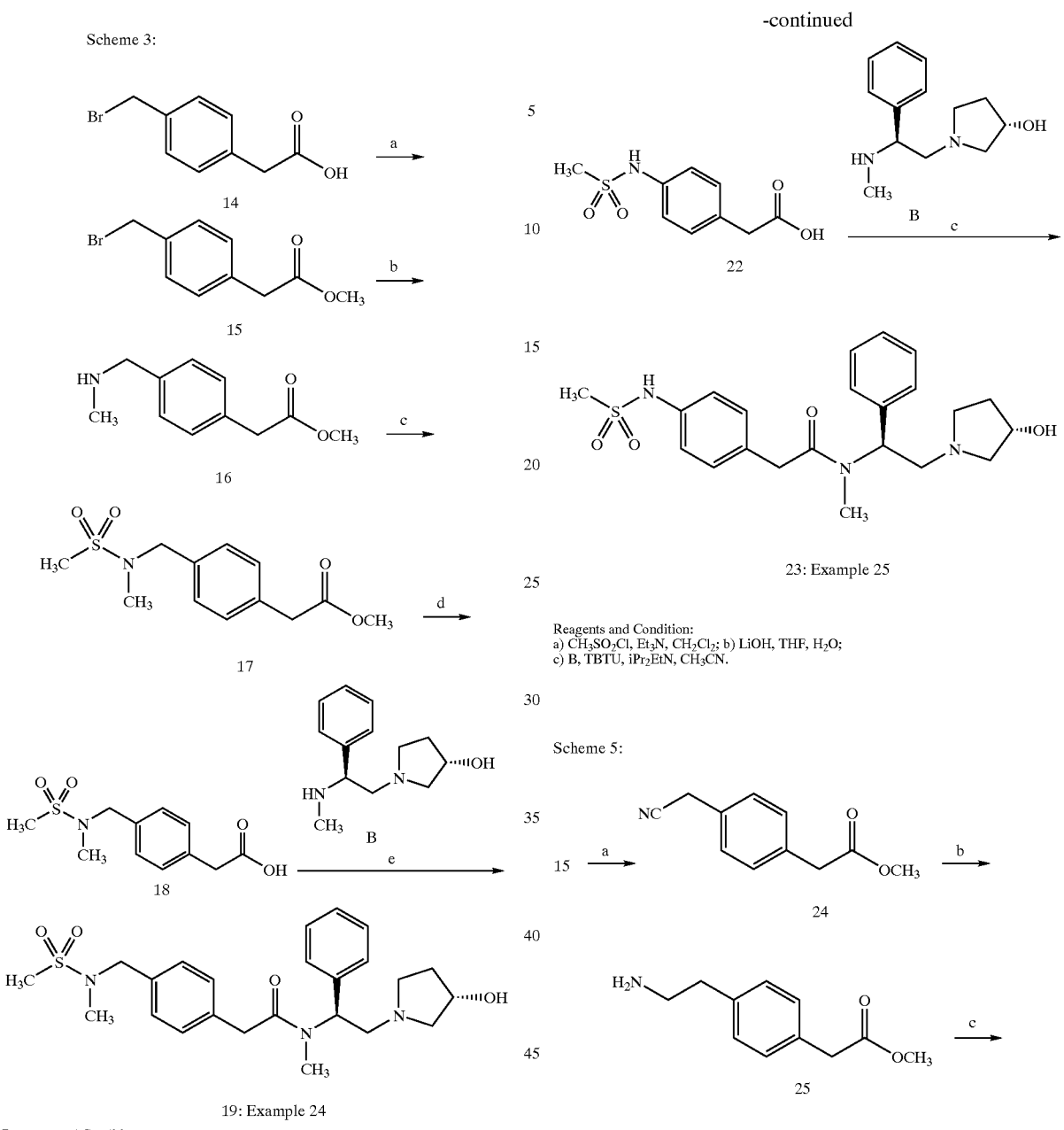
Reagents and Conditions:
a) CH$_3$OH, EDC, DMAP, THF; b) CH$_3$NH$_2$, TEA, THF; c) CH$_3$SO$_2$Cl, Et$_3$N, CH$_2$Cl$_2$; d) LiOH, THF, H$_2$O; e) B, TBTU, iPr$_2$EtN, CH$_3$CN.
Scheme 4:
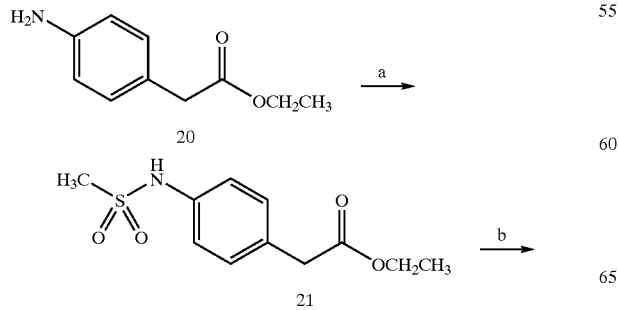
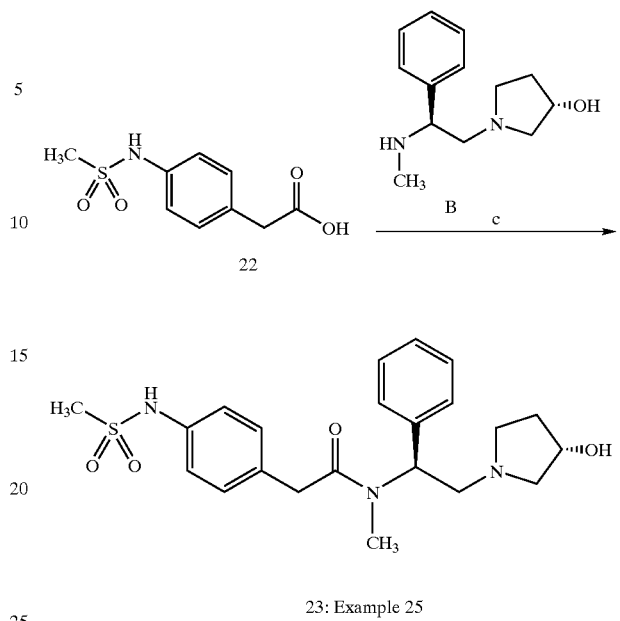
Reagents and Condition:
a) CH$_3$SO$_2$Cl, Et$_3$N, CH$_2$Cl$_2$; b) LiOH, THF, H$_2$O; c) B, TBTU, iPr$_2$EtN, CH$_3$CN.
Scheme 5:
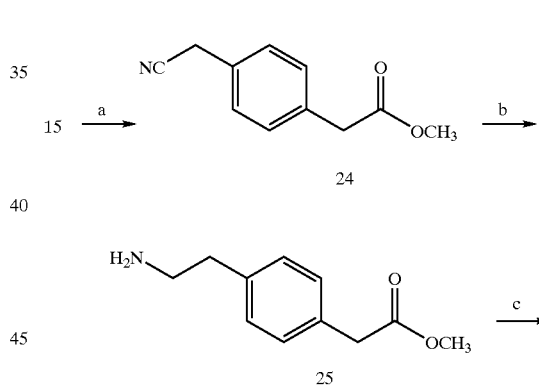

25
-continued

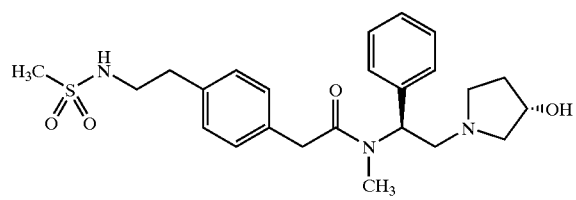

28: Example 26

Reagents and Conditions:
a) KCN, DMF; b) H₂, Pd/C, HCl, CH₃OH; c) CH₃SO₂Cl, Et₃N, CH₂Cl₂; d) LiOH, THF, H₂O; e) B, TBTU, iPr₂EtN, CH₃CN.

Scheme 6:

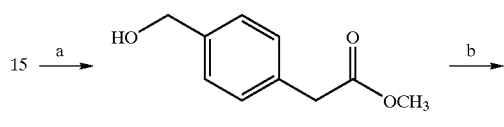

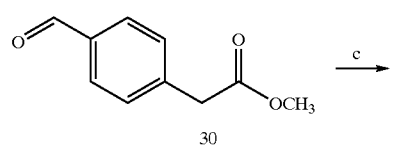

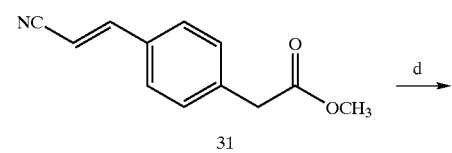

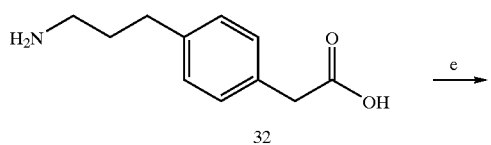

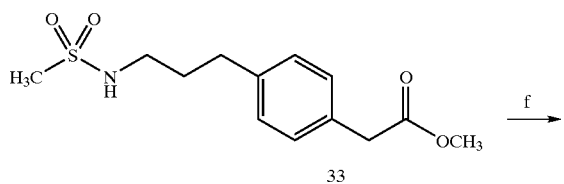

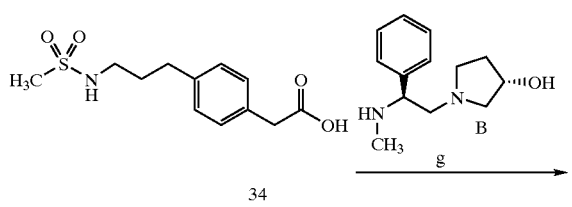

26
-continued

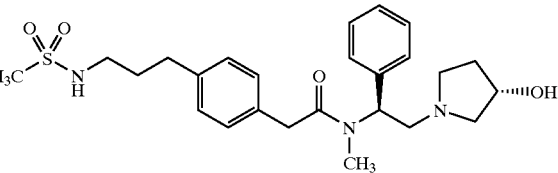

35: Example 27

Reagents and Conditions:
a) CaCO₃, Dioxane, H₂O, reflux; b) Dess-Martin Periodinane, CH₂Cl₂; c) (Ph₃)P=C—CN, Benzene, Reflux; d) H₂, Pd(OH)₂/C, HCl, CH₃OH; e) CH₃SO₂Cl, Et₃N, CH₂Cl₂; f) LiOH, THF, H₂O; g) B, TBTU, iPr₂EtN, CH₃CN.

Scheme 7a:

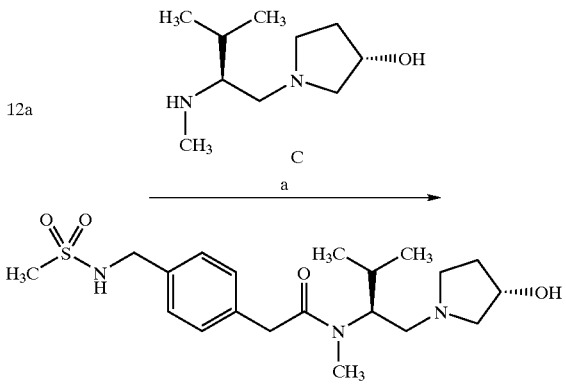

36a: Example 28

Scheme 7b:

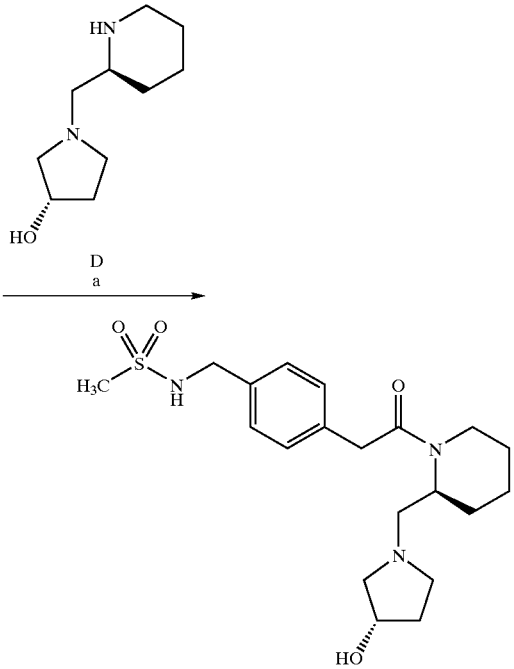

36b: Example 29

Reagents and Conditions:
a) C or D, TBTU, iPr₂EtN, CH₃CN.

The present invention will now be illustrated by reference to the following specific, non-limiting examples. Those skilled in the art of organic synthesis may be aware of still other synthetic routes to the invention compounds. The reagents and intermediates used herein are either commercially available or prepared according to standard literature procedures.

EXAMPLES

The following Examples 1 to 29 were prepared using the general procedures outlined above.

Materials: All chemicals were reagent grade and used without further purification. Analytical: thin-layer chromatography (TLC) was performed on silica gel 60 flexible backed plates (250 microns) from Alltech and visualized by UV 254 irradiation and iodine. Flash chromatography was conducted using the ISCO CombiFlash with RediSep silica gel cartridges (4 g, 12 g, 40 g, 120 g). Chromatographic elution solvent systems are reported as volume:volume ratios and all solvent systems using methanol contain 1% ammonium hydroxide. All $^1$H NMR spectra were recorded at ambient temperature on a Bruker-400 MHz spectrometer. They are reported in ppm on the $\delta$ scale, from TMS. LC-MS data were obtained using a Thermo-Finnigan Surveyor HPLC and a Thermo-Finnigan AQA MS using either positive or negative electrospray ionization. Program (positive) Solvent A: 10 mM ammonium acetate, pH 4.5, 1% acetonitrile; solvent B: acetonitrile; column: Michrom Bioresources Magic C18 Macro Bullet, detector: PDA $\lambda$=220–300 nm. Gradient: 96% A–100% B in 3.2 minutes, hold 100% B for 0.4 minutes. Program (negative) Solvent A: 1 mM ammonium acetate, pH 4.5, 1% acetonitrile; solvent B: acetonitrile; column: Michrom Bioresources Magic C18 Macro Bullet, detector: PDA $\lambda$=220–300 nm. Gradient: 96% A–100% B in 3.2 minutes, hold 100% B for 0.4 minutes.

Example 1

Preparation of [2-({methyl-[1-(S)-phenyl-2-pyrrolidin-1-yl-ethyl]-carbamoyl}-methyl)-benzyl]-carbamic acid tert-butyl ester (7a)

Step a: (2-bromo-phenyl)-acetic acid methyl ester (2a)

To a stirring solution of 1a in methanol (0.5 M) at room temperature was added concentrated sulfuric acid (0.1 eq). The reaction was heated to reflux overnight. The methanol was removed under reduced pressure. The resulting oil was dispersed in ethyl acetate and washed with saturated sodium bicarbonate (1×), dried over sodium sulfate, filtered and concentrated in vacuo to afford the product as a clear oil. (96%) $^1$H NMR (300 MHz, CDCl$_3$) $\delta$ 7.58 (m, 1H), 7.28 (m, 2H), 7.15 (m, 1H), 3.81 (s, 2H), 3.71 (s, 3H).

Step b: (2-cyano-phenyl)-acetic acid methyl ester (3a)

To a stirring solution of copper (I) cyanide (1.2 eq) in dimethylformamide (2.1 M) at room temperature was added slowly a solution of 2a in dimethylformamide (8.7 M). The reaction was heated to reflux overnight then cooled to room temperature. A solution of iron (III) chloride (1.2 eq) in H$_2$O (0.3 M) was added slowly to the vigorously stirred solution. The resulting solution was extracted with ethyl acetate (3×). The organic phases were combined then washed with brine (1×), dried over sodium sulfate, filtered, concentrated in vacuo and purified by flash chromatography (15% ethyl acetate/hexanes) to afford the product as a clear oil. (70%) $^1$H NMR (300 MHz, CDCl$_3$) $\delta$ 6.09 (m, 1H), 5.98 (m, 1H), 5.79 (m, 2H), 2.29 (s, 2H), 2.11 (s, 3H).

Step c: (2-aminomethyl-phenyl)-acetic acid methyl ester hydrochloride (4a)

To a solution of 3a in methanol (0.2 M) was added palladium, 10 weight % (dry basis) on activated carbon, wet, (0.1 eq) and concentrated hydrochloric acid (3.5 eq). The reaction mixture was shaken overnight on a Parr reactor, with hydrogen pressure equal to 70 psi. The reaction mixture was filtered through celite, concentrated in vacuo then triturated with ether. The product was obtained as a white solid. (85%) $^1$H NMR (300 MHz, DMSO-d$_6$) $\delta$ 8.66 (br s, 2H), 7.55 (m, 1H), 7.32 (m, 3H), 4.01 (m, 2H), 3.89 (s, 2H), 3.61 (s, 3H).

Step d: [2-(tert-butoxycarbonylamino-methyl)-phenyl]-acetic acid methyl ester (5a)

To a stirring solution of 4a in dichloromethane (0.4 M) at 0° C., under nitrogen, was added slowly triethylamine (2.1 eq) and a solution of di-tert-butyl dicarbonate in dichloromethane (2.0 M). The reaction was stirred at room temperature overnight. The reaction was washed with saturated sodium bicarbonate (1×) and brine (1×), dried over sodium sulfate, filtered and concentrated in vacuo to afford the product. (94%) $^1$H NMR (400 MHz, CDCl$_3$) $\delta$ 7.30 (m, 1H), 7.21 (m, 3H), 5.05 (br s, 1H), 4.31 (m, 2H), 3.66 (s, 3H), 1.50 (s, 2H), 1.44 (s, 9H).

Step e: [2-(tert-butoxycarbonylamino-methyl)-phenyl]-acetic acid (6a)

To a stirring solution of 5a in tetrahydrofuran (0.3 M) at room temperature was added a solution of lithium hydroxide monohydrate (1.2 M) in H$_2$O (0.4 M). The reaction was stirred at room temperature overnight. The tetrahydrofuran was removed under reduced pressure. The remaining aqueous phase was acidified with concentrated hydrochloric acid. The precipitated product was filtered off and dried to afford a white solid. (98%) $^1$H NMR (400 MHz, DMSO-d$_6$) $\delta$ 12.34 (br s, 1H), 7.29 (m, 1H), 7.19 (m, 4H), 4.12 (m, 2H), 3.65 (s, 2H), 1.38 (s, 9H).

Step f: [2-({methyl-[1-(S)-phenyl-2-pyrrolidin-1-yl-ethyl]-carbamoyl}-methyl)-benzyl]-carbamic acid tert-butyl ester (7a)

To a stirring solution of methyl-[1-(S)-phenyl-2-pyrrolidin-1-yl-ethyl]-amine in acetonitrile (0.3 M) at 0° C. under nitrogen was added diisopropylethylamine (2.2 eq), 6a (1.1 eq) and O-benzotriazol-1-yl-N,N,N',N'-tetramethyluronium tetrafluoroborate (TBTU) (1.1 eq). The reaction was stirred at room temperature overnight. The acetonitrile was removed under reduced pressure. The remaining oil was partitioned between ethyl acetate and saturated sodium bicarbonate. The phases were separated and the organic phase was washed with saturated sodium bicarbonate (2×), brine (1×), dried over sodium sulfate, filtered, concentrated in vacuo and purified by flash chromatography using the ISCO (1–15% gradient methanol/dichloromethane) to afford the product. (65%) $^1$H NMR (400 MHz, CDCl$_3$) $\delta$ 7.29 (m, 9H), 6.21 (m, 1H), 5.62 (m, 1H), 4.31 (m, 2H), 3.95 (m, 1H), 3.71 (m, 1H), 3.05 (m, 1H), 2.82 (m, 5H), 2.55 (m, 2H), 1.85 (m, 5H), 1.46 (s, 9H). Mass Spectral Analysis m/z=452.3 (M+H)$^+$ $t_R$=4.92 min (96%)

Example 2

Preparation of [3-({methyl-[1-(S)-phenyl-2-pyrrolidin-1-yl-ethyl]-carbamoyl}-methyl)-benzyl]-carbamic acid tert-butyl ester (7b)

Steps a–f: [3-({methyl-[1-(S)-phenyl-2-pyrrolidin-1-yl-ethyl]-carbamoyl}-methyl)-benzyl]-carbamic acid tert-butyl ester (7b)

Compound 7b was prepared by following the procedure of Example 1, Steps a–f, except 1b was substituted for 1a. Step a: (2b) (97%) $^1$H NMR (300 MHz, CDCl$_3$) $\delta$ 7.45 (m, 2H), 7.218 (m, 2H), 3.71 (s, 3H), 3.60 (s, 2H).

Step b: (3b) (70%) ¹H NMR (300 MHz, CDCl₃) δ 5.95 (m, 3H), 5.81 (m, 1H), 2.11 (s, 3H), 2.02 (s, 2H).

Step c: (4b) (91%) ¹H NMR (300 MHz, DMSO-d₆) δ 8.59 (br s, 2H), 7.39 (m, 4H), 4.01 (m, 2H), 3.69 (s, 2H), 3.61 (s, 3H).

Step d: (5b) (85%) ¹H NMR (400 MHz, CDCl₃) δ 7.25 (s, 4H), 7.15 (m, 3H), 4.97 (br s, 1H), 4.26 (m, 2H), 3.66 (s, 3H), 3.57 (s, 2H), 1.44 (s, 9H).

Step e: (6b) (97%) ¹H NMR (400 MHz, DMSO-d₆) δ 12.31 (s, 1H), 7.38 (m, 1H), 7.25 (m, 1H), 7.11 (m, 3H), 4.10 (m, 2H), 3.51 (s, 2H), 1.38 (s, 9H).

Step f: (7b) (34%) ¹H NMR (400 MHz, CDCl₃) δ 7.28 (m, 9H), 6.12 (m, 1H), 4.81 (m, 1H), 4.29 (m, 2H), 3.76 (m, 2H), 3.15 (m, 1H), 2.94 (m, 1H), 2.72 (m, 5H), 2.52 (m, 2H), 1.75 (m, 4H), 1.46 (s, 9H). Mass Spectral Analysis m/z=452.3 (M+H)⁺ t$_R$=5.04 min (96%)

Example 3

Preparation of [4-({methyl-[1-(S)-phenyl-2-pyrrolidin-1-yl-ethyl]-carbamoyl}-methyl)-benzyl]-carbamic acid tert-butyl ester (7c)

Steps a–f: [4-({methyl-[1-(S)-phenyl-2-pyrrolidin-1-yl-ethyl]-carbamoyl}-methyl)-benzyl]-carbamic acid tert-butyl ester (7c)

Compound 7c was prepared by following the procedure of Example 1, Steps a–f, except 1c was substituted for 1a.

Step a: (2c) (93%) ¹H NMR (300 MHz, CDCl₃) δ 7.45 (d, 2H), 7.19 (d, 2H), 3.71 (s, 3H), 3.59 (s, 2H).

Step b: (3c) (63%) ¹H NMR (300 MHz, CDCl₃) δ 6.08 (d, 2H), 5.85 (d, 2H), 2.11 (s, 3H), 2.09 (s, 2H).

Step c: (4c) (93%) ¹H NMR (300 MHz, DMSO-d₆) δ 8.52 (br s, 2H), 7.48 (d, 2H), 7.31 (d, 2H), 4.00 (s, 2H), 3.71 (s, 2H), 3.61 (s, 3H).

Step d: (5c) (94%) ¹H NMR (400 MHz, CDCl₃) δ 7.21 (s, 4H), 4.91 (br s, 1H), 4.26 (m, 2H), 3.66 (s, 3H), 3.57 (s, 2H), 1.44 (s, 9H).

Step e: (6c) (100%) ¹H NMR (400 MHz, DMSO-d₆) δ 7.38 (m, 1H), 7.18 (m, 4H), 4.09 (m, 2H), 3.52 (s, 2H), 1.38 (s, 9H).

Step f: (7c) (40%) ¹H NMR (400 MHz, CDCl₃) δ 7.25 (m, 9H), 6.12 (m, 1H), 4.84 (m, 1H), 4.30 (m, 2H), 3.78 (m, 2H), 3.15 (m, 1H), 2.95 (m, 1H), 2.71 (m, 5H), 2.49 (m, 2H), 1.76 (m, 4H), 1.46 (s, 9H). Mass Spectral Analysis m/z=452.3 (M+H)⁺ t$_R$=4.68 min (99%)

Example 4

Preparation of 2-(2-aminomethyl-phenyl)-N-methyl-N-[1-(S)-phenyl-2-pyrrolidin-1-yl-ethyl]-acetamide dihydrochloride (8a)

Step g: 2-(2-aminomethyl-phenyl)-N-methyl-N-[1-(S)-phenyl-2-pyrrolidin-1-yl-ethyl]-acetamide dihydrochloride (8a)

To a stirring solution of 7a in methanol (0.1 M) at 0° C. was added a solution of hydrochloric acid (5.5 eq) in ether (2.0 M). The reaction was stirred at room temperature overnight. The methanol was removed under reduced pressure and the resulting crystals were triturated with ether, filtered off and dried to afford a white solid. (99%) ¹H NMR (400 MHz, DMSO-d₆) δ 10.91 (br s, 1H), 8.21 (br s, 2H), 7.26–7.54 (m, 9H), 6.15 (m, 1H), 3.79–4.32 (m, 9H), 3.65 (m, 2H), 3.54 (m, 1H), 3.16 (m, 3H), 2.94 (s, 3H). Mass Spectral Analysis m/z=352.3 (M+H)⁺ t$_R$=3.44 min (97%)

Example 5

Preparation of 2-(3-aminomethyl-phenyl)-N-methyl-N-[1-(S)-phenyl-2-pyrrolidin-1-yl-ethyl]-acetamide dihydrochloride (8b)

Step g: 2-(3-aminomethyl-phenyl)-N-methyl-N-[1-(S)-phenyl-2-pyrrolidin-1-yl-ethyl]-acetamide dihydrochloride (8b)

Compound 8b was prepared by following the procedure of Example 4, Step g, except 7b was substituted for 7a. (90%) ¹H NMR (400 MHz, DMSO-d₆) δ 10.74 (br s, 1H), 8.34 (br s, 2H), 7.23–7.48 (m, 9H), 6.16 (m, 1H), 4.10 (m, 1H), 3.99 (m, 3H), 3.81 (m, 1H), 3.31–3.69 (m, 8H), 3.15 (m, 2H), 2.81 (s, 3H). Mass Spectral Analysis m/z=352.2 (M+H)⁺ t$_R$=2.22 min (96%)

Example 6

Preparation of 2-(4-aminomethyl-phenyl)-N-methyl-N-[1-(S)-phenyl-2-pyrrolidin-1-yl-ethyl]-acetamide dihydrochloride (8c)

Step g: 2-(4-aminomethyl-phenyl)-N-methyl-N-[1-(S)-phenyl-2-pyrrolidin-1-yl-ethyl]-acetamide dihydrochloride (8c)

Compound 8c was prepared by following the procedure of Example 4, Step g, except 7c was substituted for 7a. (93%) ¹H NMR (400 MHz, DMSO-d₆) δ 10.94 (br s, 1H), 8.44 (br s, 3H), 7.40 (m, 5H), 7.34 (m, 3H), 7.26 (m, 2H), 6.16 (m, 1H), 4.10 (m, 2H), 3.84–4.03 (m, 5H), 3.78 (m, 1H), 3.57–3.69 (m, 2H), 3.52 (m, 1H), 3.16 (m, 2H), 2.84 (s, 3H). Mass Spectral Analysis m/z=352.2 (M+H)⁺ t$_R$=3.27 min (97%)

Example 7

Preparation of 2-[2-(acetylamino-methyl)-phenyl]-N-methyl-N-[1-(S)-phenyl-2-pyrrolidin-1-yl-ethyl]-acetamide (9a)

Step h: 2-[2-(acetylamino-methyl)-phenyl]-N-methyl-N-[1-(S)-phenyl-2-pyrrolidin-1-yl-ethyl]-acetamide (9a)

To a stirring solution of 8a in dichloromethane (0.1 M) at 0° C. under nitrogen was added triethylamine (3.5 eq) and acetyl chloride (1.1 eq). The reaction was stirred at room temperature overnight. The reaction mixture was washed with saturated sodium bicarbonate (1×), brine (1×), dried over sodium sulfate, filtered, concentrated in vacuo and purified by flash chromatography using the ISCO (0–15% gradient methanol/dichloromethane) to afford the product. (70%) ¹H NMR (400 MHz, CDCl₃) δ 6.98–7.43 (m, 10H), 6.06 (m, 1H), 5.29 (m, 1H), 4.38 (m, 2H), 3.70–4.02 (m, 2H), 3.03–3.27 (m, 1H), 2.89 (s, 2H), 2.80 (s, 1H), 2.58–2.78 (m, 3H), 2.50 (br s, 1H), 1.92 (s, 3H), 1.81 (m, 1H), 1.75 (m, 3H). Mass Spectral Analysis m/z=394.3 (M+H)⁺ t$_R$=3.43 min (99%)

Example 8

Preparation of 2-[3-(acetylamino-methyl)-phenyl]-N-methyl-N-[1-(S)-phenyl-2-pyrrolidin-1-yl-ethyl]-acetamide (9c)

Step h: 2-[3-(acetylamino-methyl)-phenyl]-N-methyl-N-[1-(S)-phenyl-2-pyrrolidin-1-yl-ethyl]-acetamide (9b)

Compound 9b was prepared by following the procedure of Example 7, Step h, except 8b was substituted for 8a.

(41%) ¹H NMR (400 MHz, CDCl₃) δ 7.07–7.35 (m, 9H), 6.11 (m, 1H), 5.78 (m, 1H), 4.39 (m, 2H), 3.70–3.85, (m, 2H), 2.79–3.18 (m, 2H), 2.73 (s, 4H), 2.49 (m, 2H), 2.00 (m, 3H), 1.73 (m, 5H). Mass Spectral Analysis m/z=394.3 (M+H)⁺ $t_R$=3.30 min (95%)

Example 9

Preparation of 2-[4-(acetylamino-methyl)-phenyl]-N-methyl-N-[1-(S)-phenyl-2-pyrrolidin-1-yl-ethyl]-acetamide (9c)

Step h: 2-[4-(acetylamino-methyl)-phenyl]-N-methyl-N-[1-(S)-phenyl-2-pyrrolidin 1-yl-ethyl]-acetamide (9c)

Compound 9c was prepared by following the procedure of Example 7, Step h, except 8c was substituted for 8a. (87%) ¹H NMR (400 MHz, CDCl₃) δ 7.07–7.36 (m, 9H), 6.11 (m, 1H), 5.80 (m, 1H), 4.39 (m, 2H), 3.76 (m, 2H), 2.78–3.19 (m, 2H), 2.71 (s, 4H), 2.49 (m, 2H), 2.01 (m, 3H), 1.75 (m, 5H). Mass Spectral Analysis m/z=394.3. (M+H)⁺ $t_R$=3.13 min (99%)

Example 10

Preparation of 2-[2-(methanesulfonylamino-methyl)-phenyl]-N-methyl-N-[1-(S)-phenyl-2-pyrrolidin-1-yl-ethyl]-acetamide (10a)

Step i: 2-[2-(methanesulfonylamino-methyl)-phenyl]-N-methyl-N-[1-(S)-phenyl-2-pyrrolidin-1-yl-ethyl]-acetamide (10a)

To a stirring solution of 8a in dichloromethane (0.1 M) at 0° C. under nitrogen was added triethylamine (3.5 eq) and methanesulfonyl chloride (1.1 eq). The reaction was stirred at room temperature overnight. The reaction mixture was washed with saturated sodium bicarbonate (1×), brine (1×), dried over sodium sulfate, filtered, concentrated in vacuo and purified by flash chromatography using the ISCO (0–15% gradient methanol/dichloromethane) to afford the product. (41%) ¹H NMR (400 MHz, CDCl₃) δ 7.16–7.46 (m, 9H), 6.79 (m, 1H), 6.12 (m, 1H), 4.32 (m, 2H), 4.03 (m, 1H), 3.70 (m, 1H), 3.36–3.17 (m, 1H), 2.90 (s, 2H), 2.47–2.83 (m, 6H), 1.74 (m, 6H), 1.25 (m, 1H). Mass Spectral Analysis m/z=430.3 (M+H)⁺ $t_R$=3.70 min (96%)

Example 11

Preparation of 2-[3-(methanesulfonylamino-methyl)-phenyl]-N-methyl-N-[1-(S)-phenyl-2-pyrrolidin-1-yl-ethyl]-acetamide hydrochloride (10b)

Step i: 2-[3-(methanesulfonylamino-methyl)-phenyl]-N-methyl-N-[1-(S)-phenyl-2-pyrrolidin-1-yl-ethyl]-acetamide hydrochloride (10b)

Compound 10b was prepared by following the procedure of Example 10, Step i, except 8b was substituted for 8a. The resulting oil was dissolved in dichloromethane (0.1 M) and a solution of hydrochloric acid (5.5 eq) in ether (2.0 M) was added slowly at 0° C. The solvent was removed under reduced pressure. The resulting solid was triturated with ether then filtered off to afford the product as the hydrochloric acid salt. (49%) ¹H NMR (400 MHz, DMSO-d₆) δ 10.49 (br s, 1H), 7.18–7.60 (m, 9H), 6.16 (m, 1H), 4.03–4.15 (m, 3H), 3.86 (m, 2H), 3.51–3.68 (m, 3H), 3.14 (m, 2H), 2.84 (s, 3H), 2.78 (s, 3H), 1.99 (m, 4H)). Mass Spectral Analysis m/z=430.2 (M+H)⁺ $t_R$=1.45 min (98%)

Example 12

Preparation of 2-[4-(methanesulfonylamino-methyl)-phenyl]-N-methyl-N-[1-(S)-phenyl-2-pyrrolidin-1-yl-ethyl]-acetamide (10c)

Step i: 2-[4-(methanesulfonylamino-methyl)-phenyl]-N-methyl-N-[1-(S)-phenyl-2-pyrrolidin-1-yl-ethyl]-acetamide (10c)

Compound 10c was prepared by following the procedure of Example 10, Step i, except 8e was substituted for 8a. (44%) ¹H NMR (400 MHz, CDCl₃) δ 7.08–7.35 (m, 9H), 6.12 (m, 1H), 4.85 (m, 1H), 4.29 (m, 2H), 3.78 (m, 2H), 3.17 (m, 1H), 2.86 (s, 3H), 2.79 (s, 1H), 2.71 (s, 4H), 2.50 (m, 2H), 1.76 (m, 5H). Mass Spectral Analysis m/z=430.3 (M+H)⁺ $t_R$=3.43 min (98%)

Example 13

Preparation of N-{2-[3-(S)-hydroxy-pyrrolidin-1-yl]-1-(S)-phenyl-ethyl}-2-[4-(methanesulfonylamino-methyl)-phenyl]-N-methyl-acetamide hydrochloride (13a)

Step a: [4-(methanesulfonylamino-methyl)-phenyl]-acetic acid methyl ester (11a)

Compound 1a was prepared by following the procedure of Example 10, Step i, except 4c was substituted for 8a. The crude product was carried on without further purification. (93%)

Step b: [4-(methanesulfonylamino-methyl)-phenyl]-acetic acid (12a)

Compound 12a was prepared by following the procedure of Example 1, Step e, except 11a was substituted for 5a. (54%) Mass Spectral Analysis m/z=242.2 (M–H)⁻ $t_R$=1.47 min (96%)

Step c: N-{2-[3-(S)-hydroxy-pyrrolidin-1-yl]-1-(S)-phenyl-ethyl}-2-[4-(methane sulfonylamino-methyl)-phenyl]-N-methyl-acetamide hydrochloride (13a)

Compound 13a was prepared by following the procedure of Example 1, Step f, except 12a was substituted for 6a, 1-[2-methylamino-2-(S)-phenyl-ethyl]-pyrrolidin-3-(S)-ol dihydrochloride was substituted for methyl-[1-(S)-phenyl-2-pyrrolidin-1-yl-ethyl]-amine and diisopropylethylamine (3.3 eq) was substituted for diisopropylethylamine (2.2 eq). The resulting oil was dissolved in dichloromethane (0.1 M) and a solution of hydrochloric acid (5.5 eq) in ether (2.0 M) was added slowly at 0° C. The solvent was removed under reduced pressure. The resulting solid was triturated with ether then filtered off to afford the product as the hydrochloric acid salt. (55%) ¹H NMR (400 MHz, DMSO-d₆) δ 10.22–10.72 (m, 1H), 7.55 (m, 1H), 7.18–7.42 (m, 9H), 6.17 (m, 1H), 5.42–5.62 (m, 1H), 4.44 (m, 1H), 4.13 (m, 3H), 3.84 (m, 2H), 3.40–3.72 (m, 3H), 3.17 (m, 1H), 2.83 (s, 3H), 2.76 (m, 3H), 2.09–2.35 (m, 1H), 1.89 (m, 1H). Mass Spectral Analysis m/z=446.4 (M+H)⁺ $t_R$=3.45 min (98%)

Example 14

Preparation of 2-[4-(ethanesulfonylamino-methyl)-phenyl]-N-{2-[3-(S)-hydroxy-pyrrolidin-1-yl]-1-(S)-phenyl-ethyl}-N-methyl-acetamide hydrochloride (13b)

Steps a–c: 2-[4-(ethanesulfonylamino-methyl)-phenyl]-N-{2-[3-(S)-hydroxy-pyrrolidin-1-yl]-1-(S)-phenyl-ethyl}-N-methyl-acetamide hydrochloride (13 b)

Compound 13b was prepared by following the procedure of Example 13, Step a–c, except ethanesulfonyl chloride was substituted for methanesulfonyl chloride.

Step a: (11b) The crude product was carried on without further purification. (33%)
Step b: (12b) The crude product was carried on without further purification. (75%)
Step c: (13b) (78%) $^1$H NMR (400 MHz, DMSO-d$_6$) δ 10.21–10.55 (m, 1H), 7.60 (m, 1H), 7.18–7.42 (m, 9H), 6.17 (m, 1H), 5.43–5.62 (m, 1H), 4.44 (m, 1H), 4.11 (m, 3H), 3.84 (m, 2H), 3.44–3.72 (m, 3H), 2.91 (m, 2H), 2.75 (m, 3H), 2.07–2.35 (m, 1H), 1.89 (m, 1H), 1.13 (m, 3H). Mass Spectral Analysis m/z=460.3 (M+H)$^+$ t$_R$=1.44 min (99%)

Example 15

Preparation of N-{2-[3-(S)-hydroxy-pyrrolidin-1-yl]-1-(S)-phenyl-ethyl}-N-methyl-2-{4-[(propane-2-sulfonylamino)-methyl]-phenyl}-acetamide hydrochloride (13c)

Steps a–c: N-{2-[3-(S)-hydroxy-pyrrolidin-1-yl]-1-(S)-phenyl-ethyl}-N-methyl-2-{4-[(propane-2-sulfonylamino)-methyl]-phenyl}-acetamide hydrochloride (13c)

Compound 13c was prepared by following the procedure of Example 13, Step a–c, except propane-2-sulfonyl chloride was substituted for methanesulfonyl chloride.
Step a: (11c) The crude product was carried on without further purification. (41%)
Step b: (12c) The crude product was carried on without further purification. (65%)
Step c: (13c) (67%) $^1$H NMR (400 MHz, DMSO-d$_6$) δ 10.25–10.62 (m, 1H), 7.57 (m, 1H), 7.19–7.42 (m, 9H), 6.17 (m, 1H), 5.43–5.62 (m, 1H), 4.44 (m, 1H), 4.13 (m, 3H), 3.84 (m, 2H), 3.45–3.72 (m, 3H), 3.17 (m, 1H), 3.06 (m, 1H), 2.76 (m, 3H), 2.08–2.35 (m, 1H), 1.88 (m, 1H), 1.19 (m, 6H). Mass Spectral Analysis m/z=474.3 (M+H)$^+$ t$_R$=1.54 min (97%)

Example 16

Preparation of N-{2-[3-(S)-hydroxy-pyrrolidin-1-yl]-1-(S)-phenyl-ethyl}-N-methyl-2-{4-[(propane-1-sulfonylamino)-methyl]-phenyl}-acetamide hydrochloride (13d)

Steps a–c: N-{2-[3-(S)-hydroxy-pyrrolidin-1-yl]-1-(S)-phenyl-ethyl}-N-methyl-2-{4-[(propane-1-sulfonylamino)-methyl]-phenyl}-acetamide hydrochloride (13d)

Compound 13d was prepared by following the procedure of Example 13, Step a–c, except propane-1-sulfonyl chloride was substituted for methanesulfonyl chloride.
Step a: (11d) The crude product was carried on without further purification. (48%)
Step b: (12d) The crude product was carried on without further purification. (67%)
Step c: (13d) (2%) $^1$H NMR (400 MHz, DMSO-d$_6$) δ 10.18–10.50 (m, 1H), 7.59 (m, 1H), 7.19–7.41 (m, 9H), 6.16 (m, 1H), 5.43–5.60 (m, 1H), 4.44 (m, 1H), 4.11 (m, 3H), 3.83 (m, 2H), 3.44–3.72 (m, 3H), 3.19 (m, 1H), 2.86 (m, 2H), 2.75 (m, 3H), 2.08–2.34 (m, 1H), 1.89 (m, 1H), 1.61 (m, 2H), 0.87 (m, 3H). Mass Spectral Analysis m/z=474.2 (M+H)$^+$ t$_R$=1.56 min (97%)

Example 17

Preparation of 2-{4-[(butane-1-sulfonylamino)-methyl]-phenyl}-N-{2-[3-(S)hydroxy-pyrrolidin-1-yl]-1-(S)-phenyl-ethyl}-N-methyl-acetamide hydrochloride (23e)

Steps a–c: 2-{4-[(butane-1-sulfonylamino)-methyl]-phenyl}-N-{2-[3-(S)-hydroxy-pyrrolidin-1-yl]-1-(S)-phenyl-ethyl}-N-methyl-acetamide hydrochloride (13e)

Compound 13e was prepared by following the procedure of Example 13, Step a–c, except butane-1-sulfonyl chloride was substituted for methanesulfonyl chloride.

Step a: (11e) The crude product was carried on without further purification. (51%)
Step b: (12e) The crude product was carried on without further purification. (67%)
Step c: (13e) (76%) $^1$H NMR (400 MHz, DMSO-d$_6$) δ 10.31–10.75 (m, 1H), 7.60 (m, 1H), 7.19–7.42 (m, 9H), 6.17 (m, 1H), 5.42–5.63 (m, 1H), 4.44 (m, 1H), 4.11 (m, 3H), 3.85 (m, 2H), 3.45–3.72 (m, 3H), 3.16 (m, 1H), 2.82 (m, 2H), 2.76 (m, 3H), 2.09–2.35 (m, 1H), 1.89 (m, 1H), 1.57 (m, 2H), 1.28 (m, 2H), 0.82 (m, 3H). Mass Spectral Analysis m/z=488.3 (M+H)$^+$ t$_R$=1.70 min (97%)

Example 18

Preparation of 2-[4-(benzenesulfonylamino-methyl)-phenyl]-N-{2-[3-(S)-hydroxy-pyrrolidin-1-yl]-1-(S)-phenyl-ethyl}-N-methyl-acetamide hydrochloride (13f)

Steps a–c: 2-[4-(benzenesulfonylamino-methyl)-phenyl]-N-{2-[3-(S)-hydroxy-pyrrolidin-1-yl]-1-(S)-phenyl-ethyl}-N-methyl-acetamide hydrochloride (13f)

Compound 13f was prepared by following the procedure of Example 13, Step a–c, except benzenesulfonyl chloride was substituted for methanesulfonyl chloride.
Step a: (11f) The crude product was carried on without further purification. (42%)
Step b: (12f) The crude product was carried on without further purification. (87%)
Step c: (13f) (77%) Step c: (13e) (76%) $^1$H NMR (400 MHz, DMSO-d$_6$) δ 10.35–10.81 (m, 1H), 8.16 (m, 1H), 7.82 (m, 2H), 7.59 (m, 3H), 7.37 (m, 3H), 7.20 (m, 6H), 6.17 (m, 1H), 5.41–5.65 (m, 1H), 4.43 (m, 1H), 4.10 (m, 1H), 3.12–3.99 (m, 8H), 2.76 (m, 3H), 2.09–2.35 (m, 1H), 1.89 (m, 1H). Mass Spectral Analysis m/z=508.2 (M+H)$^+$ t$_R$=1.76 min (96%)

Example 19

Preparation of 2-{4-[(4-fluoro-benzenesulfonylamino)-methyl]-phenyl}-N-{2-[3-(S)-hydroxy-pyrrolidin-1-yl]-1-(S)-phenyl-ethyl}-N-methyl-acetamide hydrochloride (13g)

Steps a–c: 2-{4-[(4-fluoro-benzenesulfonylamino)-methyl]-phenyl}-N-{2-[3-(S)-hydroxy-pyrrolidin-1-yl]-1-(S)-phenyl-ethyl}-N-methyl-acetamide hydrochloride (13g)

Compound 13g was prepared by following the procedure of Example 13, Step a–c, except 4-fluoro-benzenesulfonyl chloride was substituted for methanesulfonyl chloride.
Step a: (11g) The crude product was carried on without further purification. (44%)
Step b: (12g) The crude product was carried on without further purification. (79%)
Step c: (13g) (71%) $^1$H NMR (400 MHz, DMSO-d$_6$) δ 10.33–10.76 (m, 1H), 8.22 (m, 1H), 7.84 (m, 2H), 7.39 (m, 3H), 7.19 (m, 6H), 6.16 (m, 1H), 5.53 (m, 1H), 4.43 (m, 1H), 4.10 (m, 1H), 3.12–3.99 (m, 8H), 2.76 (m, 3H), 2.09–2.35 (m, 1H), 1.89 (m, 1H). Mass Spectral Analysis m/z=526.2 (M+H)$^+$ t$_R$=1.80 min (96%)

Example 20

Preparation of N-{2-[3-(S)-hydroxy-pyrrolidin-1-yl]-1-(S)-phenyl-ethyl}-N-methyl-2-{4-[(toluene-4-sulfonylamino)-methyl]-phenyl}-acetamide hydrochloride (13h)

Steps a–c: N-{2-[3-(S)-hydroxy-pyrrolidin-1-yl]-1-(S)-phenyl-ethyl}-N-methyl-2-{4-[(toluene-4-sulfonylamino)-methyl]-phenyl}-acetamide hydrochloride (13h)

Compound 13h was prepared by following the procedure of Example 13, Step a–c, except 4-methyl-benzenesulfonyl chloride was substituted for methanesulfonyl chloride.

Step a: (11h) The crude product was carried on without further purification. (58%)
Step b: (12h) The crude product was carried on without further purification. (72%)
Step c: (13h) (20%) $^1$H NMR (400 MHz, DMSO-d$_6$) δ 9.40–9.93 (m, 1H), 8.04 (m, 1H), 7.69 (m, 2H), 7.38 (m, 5H), 7.19 (m, 6H), 6.15 (m, 1H), 5.40–5.61 (m, 1H), 4.37–4.51 (m, 1H), 3.19–4.15 (m, 8H), 2.69 (s, 3H), 2.38 (s, 3H), 2.27 (m, 1H), 1.91–2.11 (m, 1H), 1.84 (m, 1H). Mass Spectral Analysis m/z=522.3 (M+H)$^+$ t$_R$=1.92 min (98%)

Example 21

Preparation of N-{2-[3-(S)-hydroxy-pyrrolidin-1-yl]-1-(S)-phenyl-ethyl}-N-methyl-2-[4-(phenylmethanesulfonylamino-methyl)-phenyl]-acetamide hydrochloride (13i)

Steps a–c: N-{2-[3-(S)-hydroxy-pyrrolidin-1-yl]-1-(S)-phenyl-ethyl}-N-methyl-2-[4-(phenylmethanesulfonylamino-methyl)-phenyl]-acetamide hydrochloride Compound 13i was prepared by following the procedure of Example 13, Step a–c, except phenyl-methanesulfonyl chloride was substituted for methanesulfonyl chloride.

Step a: (11i) The crude product was carried on without further purification. (39%)
Step b: (12i) The crude product was carried on without further purification. (66%)
Step c: (13i) (29%) $^1$H NMR (400 MHz, DMSO-d$_6$) δ 10.26–10.63 (m, 1H), 7.66 (m, 1H), 7.36 (m, 8H), 7.24 (m, 6H), 6.16 (m, 1H), 5.42–5.62 (m, 1H), 4.43 (m, 1H), 4.20 (s, 2H), 4.07 (m, 3H), 3.81 (m, 2H), 3.45–3.72 (m, 3H), 3.16 (m, 1H), 2.76 (m, 3H), 2.09–2.33 (m, 1H), 1.89 (m, 1H). Mass Spectral Analysis m/z=522.2 (M+H)$^+$ t$_R$=1.78 min (96%)

Example 22

Preparation of N-{2-[3-(S)-hydroxy-pyrrolidin-1-yl]-1-(S)-Phenyl-ethyl}-N-methyl-2-{4-[(thiophene-2-sulfonylamino)-methyl]-phenyl}-acetamide hydrochloride (13j)

Steps a–c: N-[2-[3-(S)-hydroxy-pyrrolidin-1-yl]-1-(S)-Phenyl-ethyl]-N-methyl-2-{4-[(thiophene-2-sulfonylamino)-methyl]-phenyl}-acetamide hydrochloride (13j)

Compound 13j was prepared by following the procedure Example 13, Step a–c, except thiophene-2-sulfonyl chloride was substituted for methanesulfonyl chloride.

Step a: (11j) The crude product was carried on without further purification. (37%)
Step b: (12j) The crude product was carried on without further purification. (67%)
Step c: (13j) (67%) $^1$H NMR (400 MHz, DMSO-d$_6$) δ 10.29–10.69 (m, 1H), 8.36 (m, 1H), 7.91 (m, 1H), 7.59 (m, 1H), 7.37 (m, 3H), 7.19 (m, 7H), 6.16 (m, 1H), 5.43–5.62 (m, 1H), 4.44 (m, 1H), 3.12–4.16 (m, 11H), 2.75 (m, 3H), 2.09–2.35 (m, 1H), 1.89 (m, 1H). Mass Spectral Analysis m/z=514.2 (M+H)$^+$ t$_R$=1.72 min (98%)

Example 23

Preparation of 2-{4-[(3,5-dimethyl-isoxazole-4-sulfonylamino)-methyl]-phenyl}-N-{2-[3-(S)-hydroxy-pyrrolidin-1-yl]-1-(S)-phenyl-ethyl}-N-methylacetamide hydrochloride (13k)

Steps a–c: 2-{4-[(3,5-dimethyl-isoxazole-4-sulfonylamino)-methyl]-phenyl}-N-{2-[3-(S)-hydroxy-pyrrolidin-1-yl]-1-(S)-phenyl-ethyl}-N-methyl-acetamide hydrochloride (13k)

Compound 13k was prepared by following the procedure of Example 13, Step a–c, except 3,5-dimethyl-isoxazole-4-sulfonyl chloride was substituted for methanesulfonyl chloride.

Step a: (11k) The crude product was carried on without further purification. (45%)
Step b: (12k) The crude product was carried on without further purification. (71%)
Step c: (13k) (49%) $^1$H NMR (400 MHz, DMSO-d$_6$) δ 10.28–10.66 (m, 1H), 8.47 (m, 1H), 7.37 (m, 3H), 7.13–7.26 (m, 6H), 6.17 (m, 1H), 5.43–5.62 (m, 1H), 4.44 (m, 1H), 4.06 (m, 3H), 3.81 (m, 2H), 3.45–3.72 (m, 3H), 3.17 (m, 1H), 2.74 (m, 3H), 2.47 (m, 3H), 2.09–2.36 (m, 4H), 1.89 (m, 1H). Mass Spectral Analysis m/z=527.2 (M+H)$^+$ t$_R$=1.71 min (95%)

Example 24

Preparation of N-{2-[3-(S)-hydroxy-pyrrolidin-1-yl]-1-(S)-phenyl-ethyl}-2-{4-[(methanesulfonyl-methyl-amino)-methyl]-phenyl}-N-methyl-acetamide hydrochloride (19)

Step a: (4-bromomethyl-phenyl)-acetic acid methyl ester (15)

To a stirring solution of 14 in tetrahydrofuran (0.6 M) at 0° C. under nitrogen was added dimethylaminopyridine (0.2 eq), methanol (2.2 eq) and 1-[3-(dimethylamino)propyl]-3-ethylcarbodiimide hydrochloride (2.2 eq). The reaction was stirred at room temperature overnight. The tetrahydrofuran was removed under reduced pressure. The resulting oil was partitioned between ethyl acetate and saturated sodium bicarbonate. The phases were separated and the organic phase was washed with saturated sodium bicarbonate (1×), 1N hydrochloric acid (1×), brine (1×), dried over sodium sulfate, filtered and concentrated in vacuo to afford the product. (58%) $^1$H NMR (400 MHz, DMSO-d$_6$) δ 7.38 (d, 2H), 7.27 (d, 2H), 4.75 (s, 2H), 3.69 (s, 2H), 3.61 (s, 3H).

Step b: (4-methylaminomethyl-phenyl)-acetic acid methyl ester (16)

To a stirring solution of 15 in tetrahydrofuran (0.4 M) at room temperature under nitrogen was added methylamine (7.5 eq) and triethylamine (12.0 eq). The reaction was stirred at room temperature overnight. The tetrahydrofuran was removed under reduced pressure and the resulting oil was diluted with H$_2$O. The aqueous layer was acidified with 6N hydrochloric acid, extracted with ethyl acetate (3×), made basic with saturated sodium bicarbonate and extracted with dichloromethane (3×). The dichloromethane was dried over sodium sulfate, filtered and concentrated in vacuo to afford the product. (66%) $^1$H NMR (400 MHz, CDCl$_3$) δ 7.31 (d, 2H), 7.25 (d, 2H), 3.77 (s, 2H), 3.69 (s, 3H), 3.62 (s, 2H), 2.45 (s, 3H).

Step c: {4-[(methanesulfonyl-methyl-amino)-methyl]-phenyl}-acetic acid methyl ester (7)

Compound 17 was prepared by following the procedure of Example 10, Step i, except 16 was substituted for 8a. (65%) $^1$H NMR (400 MHz, CDCl$_3$) δ 7.30 (m, 4H), 4.29 (s, 2H), 3.70 (s, 3H), 3.63 (s, 2H), 2.84 (s, 3H), 2.77 (s, 3H).

Step d: {4-[(methanesulfonyl-methyl-amino)-methyl]-phenyl}-acetic acid (18)

Compound 18 was prepared by following the procedure of Example 1, Step e, except 17 was substituted for 5a. (74%) $^1$H NMR (400 MHz, DMSO-d$_6$) δ 12.32 (s, 1H), 7.27 (s, 4H), 4.20 (s, 2H), 3.57 (s, 2H), 2.94 (s, 3H), 2.65 (s, 3H).

Step e: N-{2-[3-(S)-hydroxy-pyrrolidin-1-yl]-1-(S)-phenyl-ethyl}-2-{4-[(methanesulfonyl-methyl-amino)-methyl]-phenyl}-N-methyl-acetamide hydrochloride (19)

Compound 19 was prepared by following the procedure of Example 13, Step c, except 18 was substituted for 12a. (62%) $^1$H NMR (400 MHz, DMSO-d$_6$) δ 10.33–10.76 (m, 1H), 7.20–7.41 (m, 9H), 6.17 (m, 1H), 5.37–5.80 (m, 1H), 4.42 (m, 1H), 4.21 (m, 2H), 4.10 (m, 1H), 3.13–3.97 (m, 6H), 2.94 (s, 3H), 2.78 (m, 3H), 2.65 (s, 3H), 2.10–2.36 (m, 1H), 1.88 (m, 1H). Mass Spectral Analysis m/z=460.2 (M+H)$^+$ $t_R$=1.55 min (99%)

Example 25

Preparation of N-{2-[3-(S)-hydroxy-pyrrolidin-1-yl]-1-(S)-phenyl-ethyl}-2-(4-methanesulfonylamino-phenyl)-N-methyl-acetamide hydrochloride (23)

Step a: (4-methanesulfonylamino-phenyl)-acetic acid ethyl ester (21)

Compound 21 was prepared by following the procedure of Example 10, Step i, except 20 was substituted for 8a. The crude product was carried on without further purification. (89%)

Step b: (4-Methanesulfonylamino-phenyl)-acetic acid (22)

Compound 22 was prepared by following the procedure of Example 1, Step e, except 21 was substituted for 5a. (68%) $^1$H NMR (400 MHz, DMSO-d$_6$) δ 12.31 (s, 1H), 9.68 (s, 1H), 7.22 (d, 2H), 7.14 (d, 2H), 3.52 (s, 2H), 2.96 (s, 3H).

Step c: N-{2-[3-(S)-hydroxy-pyrrolidin-1-yl]-1-(S)-phenyl-ethyl}-2-(4-methanesulfonylamino-phenyl)-N-methyl-acetamide hydrochloride (23)

Compound 23 was prepared by following the procedure of Example 13, Step c, except 22 was substituted for 12a. (50%) $^1$H NMR (400 MHz, DMSO-d$_6$) δ 10.30–10.70 (m, 1H), 9.65 (m, 1H), 7.11–7.43 (m, 9H), 6.16 (m, 1H), 4.43 (m, 1H), 4.09 (m, 1H), 3.44–3.94 (m, 5H), 3.16 (m, 1H), 2.96 (s, 3H), 2.77 (d, 3H), 2.69 (s, 1H), 2.09–2.35 (m, 1H), 1.88 (m, 1H). Mass Spectral Analysis m/z=432.2 (M+H)$^+$ $t_R$=1.35 min (96%)

Example 26

Preparation of N-{2-[3-(S)-hydroxy-pyrrolidin-1-yl]-1-(S)-phenyl-ethyl}-2-[4-(2-methanesulfonylamino-ethyl)-phenyl]-N-methyl-acetamide hydrochloride (28)

Step a: (4-cyanomethyl-phenyl)-acetic acid methyl ester (24)

To a stirring solution of 15 in dimethylformamide (0.3 M) at room temperature under nitrogen was added potassium cyanide (1.2 eq). The reaction was stirred at room temperature overnight. The reaction was diluted with H$_2$O then extracted with ethyl acetate (3×). The organic phases were combined, washed with saturated sodium bicarbonate (1×), brine (1×), dried over sodium sulfate, filtered and concentrated in vacuo to afford the product. (26%) $^1$H NMR (400 MHz, CDCl$_3$) δ 7.30 (s, 4H), 3.74 (s, 2H), 3.70 (s, 3H) 3.64 (s, 2H).

Step b: [4-(2-amino-ethyl)-phenyl]-acetic acid methyl ester hydrochloride (25)

Compound 25 was prepared by following the procedure of Example 1, Step c, except 24 was substituted for 3a. (59%) $^1$H NMR (400 MHz, DMSO-d$_6$) δ 8.11 (br s, 3H), 7.22 (s, 4H), 3.66 (s, 2H), 3.60 (s, 3H), 3.00 (m, 2H), 2.88 (m, 2H).

Step c: [4-(2-methanesulfonylamino-ethyl)-phenyl]-acetic acid methyl ester (26)

Compound 26 was prepared by following the procedure of Example 10, Step i, except 25 was substituted for 8a. (99%) $^1$H NMR (400 MHz, CDCl$_3$) δ 7.24 (d, 2H), 7.18 (d, 2H), 4.32 (m, 1H), 3.70 (s, 3H), 3.61 (s, 2H), 3.39 (m, 2H), 2.84 (m, 5H).

Step d: [4-(2-methanesulfonylamino-ethyl)-phenyl]-acetic acid (27)

Compound 27 was prepared by following the procedure of Example 1, Step e, except 26 was substituted for 5a. (57%) $^1$H NMR (400 MHz, DMSO-d$_6$) δ 12.29 (br s, 1H), 7.18 (s, 4H), 7.09 (m, 1H), 3.52 (s, 2H), 3.15 (m, 2H), 2.83 (m, 3H), 2.74 (m, 2H)

Step e: N-{2-[3-(S)-hydroxy-pyrrolidin-1-yl]-1-(S)-phenyl-ethyl}-2-[4-(2-methanesulfonylamino-ethyl)-phenyl]-N-methyl-acetamide hydrochloride (28)

Compound 28 was prepared by following the procedure of Example 13, Step c, except 27 was substituted for 12a. (26%) $^1$H NMR (400 MHz, DMSO-d$_6$) δ 10.25–10.68 (m, 1H), 7.38 (m, 3H), 7.19 (m, 6H), 7.11 (m, 1H), 6.17 (m, 1H), 5.42–5.63 (m, 1H), 4.44 (m, 1H), 4.07 (m, 1H), 3.78 (m, 2H), 3.44–3.72 (m, 3H), 3.16 (m, 3H), 2.81 (s, 3H), 2.75 (m, 5H), 2.08–2.35 (m, 1H), 1.88 (m, 1H). Mass Spectral Analysis m/z=460.2 (M+H)$^+$ $t_R$=1.50 min (97%)

Example 27

Preparation of N-{2-[3-(S)-hydroxy-pyrrolidin-1-yl]-1-(S)-phenyl-ethyl}-2-[4-(3-methanesulfonylamino-propyl)-phenyl]-N-methyl-acetamide hydrochloride (35)

Step a: (4-hydroxymethyl-phenyl)-acetic acid methyl ester (29)

To a stirring solution of 15 in dioxane (0.4 M) at room temperature under nitrogen was added calcium carbonate (5.5 eq) and H$_2$O (0.8 M). The reaction was refluxed overnight then vacuum filtered. The dioxane was removed under reduced pressure. The reaction mixture was diluted with H$_2$O then extracted with dichloromethane (3×). The organic phases were combined, dried over sodium sulfate, filtered and concentrated in vacuo to afford the product. (77%) $^1$H NMR (400 MHz, CDCl$_3$) δ 7.33 (d, 2H), 7.27 (d, 2H), 4.67 (s, 2H), 3.69 (s, 3H), 3.63 (s, 2H), 1.78 (br s, 1H).

Step b: (4-formyl-phenyl)-acetic acid methyl ester (30)

To a stirring solution of Dess-Martin Periodinane (1.5 eq) in dichloromethane (0.3 M) at room temperature under nitrogen was added a solution of 29 in dichloromethane (0.2 M). After 4 hours the reaction was diluted with ether (0.1 M). The reaction mixture was then poured into a solution of sodium thiosulfate (10.5 eq) in saturated sodium bicarbonate (0.5 M) and stirred for 30 minutes. The phases were separated and the organic phase was washed with saturated sodium bicarbonate (1×), H$_2$O (1×) and brine (1×) then dried over sodium sulfate, filtered and concentrated in vacuo to afford the product. (94%) $^1$H NMR (400 MHz, CDCl$_3$) δ 10.00 (s, 1H), 7.86 (d, 2H), 7.46 (d, 2H), 3.72 (m, 5H).

Step c: [4-(2-cyano-vinyl)-phenyl]-acetic acid methyl ester (31)

To a stirring solution of 30 in benzene (0.4 M) at room temperature under nitrogen was added (triphenylphosphoranylidene)acetonitrile (1.1 eq). The reaction was refluxed overnight. The benzene was removed under reduced pressure. The resulting oil was dissolved in ethyl acetate and washed with 1N hydrochloric acid (1×), saturated sodium bicarbonate (1×) and brine (1×) then dried over sodium sulfate, filtered, concentrated in vacuo and purified by flash chromatography using the ISCO (0–15% gradient methanol/dichloromethane). (98%) $^1$H NMR (400 MHz, CDCl$_3$) δ 7.31–7.44 (m, 5H), 5.87 (d, 1H), 3.71 (s, 3H), 3.66 (s, 2H).

Step d: [4-(3-amino-propyl)-phenyl]-acetic acid methyl ester hydrochloride (32)

Compound 32 was prepared by following the procedure of Example 1, Step c, except 31 was substituted for 3a and palladium hydroxide, 20 weight % (dry basis) on activated carbon, wet, was substituted for palladium, 10 weight % (dry basis) on activated carbon, wet. (70%) $^1$H NMR (400 MHz, DMSO-d$_6$) δ 7.97 (br s, 3H), 7.18 (m, 4H), 3.64 (s, 2H), 3.61 (s, 3H), 3.76 (m, 2H), 2.76 (m, 2H), 2.62 (m, 2H), 1.84 (m, 2H).

Step e: [4-(3-methanesulfonylamino-propyl)-phenyl]-acetic acid methyl ester (33)

Compound 33 was prepared by following the procedure of Example 10, Step i, except 32 was substituted for 8a. (66%) $^1$H NMR (400 MHz, CDCl$_3$) δ 7.21 (d, 2H), 7.14 (d, 2H), 4.47 (m, 1H), 3.69 (s, 3H), 3.60 (s, 2H), 3.14 (m, 2H), 2.93 (s, 3H), 2.67 (m, 2H), 1.89 (m, 2H).

Step f: [4-(3-methanesulfonylamino-propyl)-phenyl]-acetic acid (34)

Compound 34 was prepared by following the procedure of Example 1, Step e, except 33 was substituted for 5a. (65%) $^1$H NMR (400 MHz, DMSO-d$_6$) δ 12.26 (s, 1H), 7.15 (m, 4H), 7.01 (m, 1H), 3.51 (s, 2H), 2.94 (m, 2H), 2.87 (s, 3H), 2.59 (m, 2H), 1.73 (m, 2H).

Step g: N-{2-[3-(S)-hydroxy-pyrrolidin-1-yl]-1-(S)-phenyl-ethyl}-2-[4-(3-methanesulfonylamino-propyl)-phenyl]-N-methyl-acetamide hydrochloride (35)

Compound 35 was prepared by following the procedure of Example 13, Step c, except 34 was substituted for 12a. (50%) $^1$H NMR (400 MHz, DMSO-d$_6$) δ 10.07–10.25 (m, 1H), 7.36 (m, 3H), 7.16 (m, 6H), 7.04 (m, 1H), 6.16 (m, 1H), 5.43–5.60 (m, 1H), 4.44 (m, 1H), 4.07 (m, 1H), 3.54–3.84 (m, 5H), 2.94 (m, 2H), 2.88 (s, 3H), 2.73 (d, 3H), 2.59 (m, 2H), 2.06–2.35 (m, 1H), 1.88 (m, 1H) 1.74 (m, 2H). Mass Spectral Analysis m/z=474.2 (M+H)$^+$ t$_R$=1.59 min (100%)

Example 28

Preparation of N-{1-[3-(S)-hydroxy-pyrrolidin-1-ylmethyl]-2-methyl-(S)-propyl}-2-[4-(methanesulfonylamino-methyl)-phenyl]-N-methyl-acetamide trifluoroacetate (36a)

Step a: N-{1-[3-(S)-hydroxy-pyrrolidin-1-ylmethyl]-2-methyl-(S)-propyl}-2-[4-(methanesulfonylamino-methyl)-phenyl]-N-methyl-acetamide trifluoroacetate (36a)

Compound 36a was prepared by following the procedure of Example 1, Step f, except 12a was substituted for 6a and 1-(3-methyl-2-(S)-methylamino-butyl)-pyrrolidin-3-(S)-ol was substituted for methyl-[1-(S)-phenyl-2-pyrrolidin-1-yl-ethyl]-amine. The resulting oil was purified using LC-Prep to afford the product as the trifluoroacetic acid salt. (5%) $^1$H NMR (400 MHz, CDCl$_3$) δ 9.85–11.08 (m, 1H), 8.21 (m, 1H), 7.05–7.35 (m, 5H), 6.46 (m, 1H), 4.97–5.47 (m, 1H), 4.00–4.70 (m, 5H), 3.48–3.94 (m, 3H), 3.10–3.44 (m, 2H), 2.66–3.01 (m, 6H), 1.57–2.42 (m, 3H), 0.57–1.03 (m, 5H). Mass Spectral Analysis m/z=412.2 (M+H)$^+$ t$_R$=1.19 min (96%)

Example 29

Preparation of N-[4-(2-{2-[3-(S)-hydroxy-pyrrolidin-1-ylmethyl]-(S)-piperidin-1-yl}-2-oxo-ethyl)-benzyl]-methanesulfonamide hydrochloride trifluoroacetate (36b)

Step a: N-[4-(2-{2-[3-(S)-hydroxy-pyrrolidin-1-ylmethyl]-(S)-piperidin-1-yl}-2-oxo-ethyl)-benzyl]-methanesulfonamide trifluoroacetate (36b)

Compound 36b was prepared by following the procedure of Example 1, Step f, except 12a was substituted for 6a and 1-piperidin-2-(S)-ylmethyl-pyrrolidin-3-(S)-ol was substituted for methyl-[1-(S)-phenyl-2-pyrrolidin-1-yl-ethyl]-amine. The resulting oil was purified using LC-Prep to afford the product as the trifluoroacetic acid salt. (14%) $^1$H NMR (400 MHz, DMSO-d$_6$) δ 9.24–9.72 (m, 1H), 7.54 (m, 1H), 7.19–7.32 (m, 4H), 4.97 (m, 1H), 4.32-4.45 (m, 2H), 4.13 (d, 1H), 3.78 (m, 4H), 3.62 (m, 3H), 3.36 (m, 1H), 3.15 (m, 4H), 2.84 (s, 3H), 1.95–2.28 (m, 1H), 1.74–1.95 (m, 1H), 1.40–1.63 (m, 4H), 1.02 (m, 1H). Mass Spectral Analysis m/z=410.2 (M+H)$^+$ t$_R$=1.08 min (98%)

The compounds of the invention (Examples 11 to 29), identified by their chemical name and molecular weight, are shown in Table 1.

TABLE 1

| Example | Name | [M + H]$^+$ |
|---|---|---|
| 11 | 2-[3-(methanesulfonylamino-methyl)-phenyl]-N-methyl-N-[1-(S)-phenyl-2-pyrrolidin-1-yl-ethyl]-acetamide | 430 |
| 12 | 2-[4-(methanesulfonylamino-methyl)-phenyl]-N-methyl-N-[1-(S)-phenyl-2-pyrrolidin-1-yl-ethyl]-acetamide | 430 |
| 13 | N-{2-[3-(S)-hydroxy-pyrrolidin-1-yl]-1-(S)-phenyl-ethyl}-2-[4-(methanesulfonylamino-methyl)-phenyl]-N-methyl-acetamide | 446 |
| 14 | 2-[4-(ethanesulfonylamino-methyl)-phenyl]-N-{2-[3-(S)-hydroxy-pyrrolidin-1-yl]-1-(S)-phenyl-ethyl}-N-methyl-acetamide | 460 |
| 15 | N-{2-[3-(S)-hydroxy-pyrrolidin-1-yl]-1-(S)-phenyl-ethyl}-N-methyl-2-{4-[(propane-2-sulfonylamino)-methyl]-phenyl}-acetamide | 474 |
| 16 | N-{2-[3-(S)-hydroxy-pyrrolidin-1-yl]-1-(S)-phenyl-ethyl}-N-methyl-2-{4-[(propane-1-sulfonylamino)-methyl]-phenyl}-acetamide | 474 |
| 17 | 2-{4-[(butane-1-sulfonylamino)-methyl]-phenyl}-N-{2-[3-(S)-hydroxy-pyrrolidin-1-yl]-1-(S)-phenyl-ethyl}-N-methyl-acetamide | 488 |
| 18 | 2-[4-(benzenesulfonylamino-methyl)-phenyl]-N-{2-[3-(S)-hydroxy-pyrrolidin-1-yl]-1-(S)-phenyl-ethyl}-N-methyl-acetamide | 508 |
| 19 | 2-{4-[(4-fluoro-benzenesulfonylamino)-methyl]-phenyl}-N-{2-[3-(S)-hydroxy-pyrrolidin-1-yl]-1-(S)-phenyl-ethyl}-N-methyl-acetamide | 526 |
| 20 | N-{2-[3-(S)-hydroxy-pyrrolidin-1-yl]-1-(S)-phenyl-ethyl}-N-methyl-2-{4-[(toluene-4-sulfonylamino)-methyl]-phenyl}-acetamide | 522 |
| 21 | N-{2-[3-(S)-hydroxy-pyrrolidin-1-yl]-1-(S)-phenyl-ethyl}-N-methyl-2-[4-(phenylmethanesulfonylamino-methyl)-phenyl]-acetamide | 522 |
| 22 | N-{2-[3-(S)-hydroxy-pyrrolidin-1-yl]-1-(S)-Phenyl-ethyl}-N-methyl-2-{4-[(thiophene-2-sulfonylamino)-methyl]-phenyl}-acetamide | 516 |
| 23 | 2-{4-[(3,5-dimethyl-isoxazole-4-sulfonylamino)-methyl]-phenyl}-N-{2-[3-(S)-hydroxy-pyrrolidin-1-yl]-1-(S)-phenyl-ethyl}-N-methyl-acetamide | 527 |
| 24 | N-{2-[3-(S)-hydroxy-pyrrolidin-1-yl]-1-(S)-phenyl-ethyl}-2-{4-[(methanesulfonyl-methyl-amino)-methyl]-phenyl}-N-methyl-acetamide | 460 |
| 25 | N-{2-[3-(S)-hydroxy-pyrrolidin-1-yl]-1-(S)-phenyl-ethyl}-2-(4-methanesulfonylamino-phenyl)-N-methyl-acetamide | 432 |
| 26 | N-{2-[3-(S)-hydroxy-pyrrolidin-1-yl]-1-(S)-phenyl-ethyl}-2-[4-(2-methanesulfonylamino-ethyl)-phenyl]-N-methyl-acetamide | 460 |
| 27 | N-{2-[3-(S)-hydroxy-pyrrolidin-1-yl]-1-(S)-phenyl-ethyl}-2-[4-(3-methanesulfonylamino-propyl)-phenyl]-N-methyl-acetamide | 474 |
| 28 | N-{1-[3-(S)-hydroxy-pyrrolidin-1-ylmethyl]-2-methyl-(S)-propyl}-2-[4-(methanesulfonylamino-methyl)-phenyl]-N-methyl-acetamide | 412 |

TABLE 1-continued

| Example | Name | [M + H]+ |
|---|---|---|
| 29 | N-[4-(2-{2-[3-(S)-hydroxy-pyrrolidin-1-ylmethyl]-(S)-piperidin-1-yl}-2-oxo-ethyl)-benzyl]-methanesulfonamide | 410 |

Biological Methods
Receptor Binding and Functional Assays

The potencies of the compounds of the invention were determined by testing the ability of a range of concentrations of each compound to inhibit the binding of the non-selective opioid antagonist, [$^3$H]diprenorphine, to the cloned human μ, κ, and δ opioid receptors, expressed in separate cell lines. $IC_{50}$ values were obtained by nonlinear analysis of the data using GraphPad Prism version 3.00 for Windows (GraphPad Software, San Diego). $K_i$ values were obtained by Cheng-Prusoff corrections of $IC_{50}$ values.

The receptor binding method was a modification of the method of K. Raynor et al. (*Mol. Pharmacol.*, 45, 330–334, 1994). After dilution in buffer A and homogenization as before, membrane proteins (10–80 μg) in 250 μL were added to mixtures containing test compound and [$^3$H] diprenorphine (0.5 to 1.0 nM, 40,000 to 50,000 dpm) in 250 μL of buffer A in 96-well deep-well polystyrene titer plates (Beckman). After incubation at room temperature for one hour, the samples were filtered through GF/B filters that had been presoaked in a solution of 0.5% (w/v) polyethylenimine and 0.1% (w/v) bovine serum albumin in water. The filters were rinsed 4 times with 1 mL of cold 50 mM Tris HCl, pH 7.8 and radioactivity remaining on the filters determined by scintillation spectroscopy. Nonspecific binding was determined by the minimum values of the titration curves and was confirmed by separate assay wells containing 10 μM naloxone. $K_i$ values were determined by Cheng-Prusoff corrections of $IC_{50}$ values derived from nonlinear regression fits of 12 point titration curves using GraphPad Prism® version 3.00 for Windows (GraphPad Software, San Diego, Calif.).

To determine the equilibrium dissociation constant for the inhibitors ($K_i$), radioligand bound (cpm) in the presence of various concentrations of test compounds was measured. The concentration to give half-maximal inhibition ($EC_{50}$) of radioligand binding was determined from a best nonlinear regression fit to the following equation, $$Y = \text{Bottom} + \frac{(\text{Top} - \text{Bottom})}{1 + 10^{X - LogEC50}}$$

where Y is the amount of radioligand bound at each concentration of test compound;
Bottom is the calculated amount of radioligand bound in the presence of an infinite concentration of test compound;
Top is the calculated amount of radioligand bound in the absence of test compound;
X is the logarithm of the concentration of test compound; and
$LogEC_{50}$ is the log of the concentration of test compound where the amount of radioligand bound is half-way between Top and Bottom.

The nonlinear regression fit was performed using the program Prism® (GraphPad Software, San Diego, Calif.). The $K_i$ values were then determined from the $EC_{50}$ values by the following equation, $$K_i = \frac{EC_{50}}{1 + \frac{[\text{ligand}]}{K_d}}$$

where [ligand] is the concentration of radioligand; and
$K_d$ is the equilibrium dissociation constant for the radioligand.

The potencies of the agonists were assessed by their abilities to stimulate [$^{35}$S]GTPγS binding to membranes containing the cloned human κ receptors.

To determine the $EC_{50}$ value, which was the concentration to give half-maximal stimulation of [$^{35}$S]GTPγS binding, the amount of [$^{35}$S]GTPγS bound in the presence of various concentrations of agonists was measured. The $EC_{50}$ value was then determined.

Inhibition of CYP2D6 Catalyzed Conversion of MAMC to HAMC
Materials

Microsomes containing baculovirus expressed human recombinant CYP2D6 and MAMC were purchased from BD Biosciences. The method is a modification of the method provided by BD Biosciences.
Buffers and Solutions:
Assay Buffer=50 mM $KPO_4$, 15 μg/mL $NADP^+$, 0.30 mg/mL glucose-6-phosphate, 0.20 mg/mL $MgCl_2$, 0.96 U/mL glucose-6-phosphate dehydrogenase, 2.5 μM MAMC, pH 7.4.
Dilution Buffer=50 mM $KPO_4$, pH 7.4
Enzyme Buffer=150 mM $KPO_4$, pH 7.4
Stop Solution=80% acetonitrile, 20% 0.5 M Tris Base
Procedure:

The assays were done in black 96 well plates (VWR Cat# 22221-572) and contained: 40 μL assay buffer, 10 μL test compound in dilution buffer and 50 μL of 10–15 pmol/mL CYP2D6 in enzyme buffer. Final concentrations: (100 mM $KPO_4$, pH 7.4, 7.9 μM $NADP^+$, 0.36 mM glucose-6-phosphate, 0.4 mM $MgCl_2$, 0.38 U/mL glucose-6-phosphate dehydrogenase, 1 μM MAMC (BD Biosciences), 0.5 pmol CYP2D6 (BD Biosciences))

For large experiments, assay buffer and test compound were added using the MiniTrak IV (Packard Biosciences), otherwise they were added using 25–250 μL and 5–100 μL 8 channel electronic pipettors (BioHit). CYP2D6 was added using 25–250 μL 8 channel electronic pipettor.
Test Compound Titrations are done in either 96 well deep-well plates (Beckman) or 96 well microtiter plates (Costar), an initial dilution in dilution buffer is prepared from stock solutions in DMSO to start either 8 (1:6) or 12 (1:3.15) serial dilutions. For 1:6 dilutions, 50 μL for each dilution is transferred to 250 μL dilution buffer. For 1:3.15 dilutions, 50 μL for each dilution is transferred to 108 μL dilution buffer. Further details on concentrations will be provided in each experiment. Titrations are done using either 25–250 μL 8 channel electronic pipettor, 30–300 μL 12 channel manual pipettor (Spectrum), or the Multiprobe II. For screening, dilution plates are prepared in dilution buffer in 96 well microtiter plates from masterplates in 100% DMSO using the Multiprobe II or MiniTrak IV. After assay buffer and test compound has been added, the plates and the enzyme buffer are prewarmed at 37° C. for 15 minutes. After prewarming, CYP2D6 is added to then enzyme buffer and then added to the assay plate using 25–250 μL 8 channel electronic pipettor and the plates are incubated for 15 minutes at 37° C. After incubation, 50 μL stop solution is added using 25–250 μL 8 channel electronic pipettor. The plates are then counted on the Fusion (Packard Biosciences) for 4 sec/well using and excitation filter of 390 nm and an emission filter of 460 nm, intensity setting of 1, high detector sensitivity.
Data Analysis:
% Inhibition Non-specific relative fluorescent units (RFU) are determined in the presence of 10 $\mu$M quinidine in wells A1, B1, and C1 of each plate and total RFU determined in wells D1, E1, F1 in the absence of test compound. Specific HAMC production is the difference between total and nonspecific. For each compound, a percent inhibition of HAMC production is calculated by:

% $I=(1-(A/B))*100$ where A=cpm specifically bound for test compound
   B=cpm specifically bound in the absence of test compound For experiments where the plates are registered in the biological database, % I is determined automatically by the biological database.
Titrations $IC_{50}$'s are calculated using nonlinear regression to a one-site model using GraphPad Prism or a VB algorithm fitting the data to that equation.
Inhibition of CYP2C9 and CYP3A4

These assays were carried out as described using CYP2C9 and CYP3A4 conversion of dibenzylfluorescein (DBF) to fluorescein (F).

The opioid receptor ($\kappa$, $\mu$, $\delta$) binding data, in vitro agonist activity ($\kappa$) and Cytochrome P450 (CYP2D6, CYP2C9 and CYP3A4) data of Examples 11 to 29 is shown in Table 2.

at the $\mu$, $\delta$ or $\kappa$ opioid receptors. Examples 11 to 29 were investigated to evaluate their capacity to inhibit the catalytic activity of the major drug metabolizing hepatic cytochrome P450 enzymes (CYP2D6, CYP3A4, CYP2C9) found in humans. This study led to the identification of several compounds (Examples 14, 15, 16, 24, 26, 27, 28 and 29) that are potent and selective K agonists and metabolically stable in regard to their activity toward the cytochrome P450.

The disclosures of each patent, patent application and publication cited or described in this document are hereby incorporated herein by reference, in their entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed:

1. A compound of Formula I:

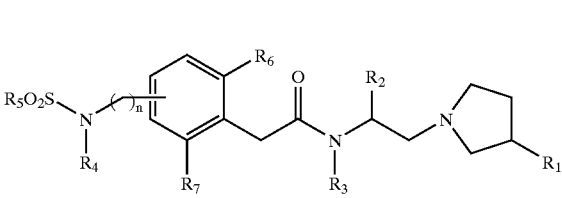

TABLE 2

| Example | $K_i(\kappa)$ (nM) | $EC_{50}(\kappa)$ (nM) | $K_i(\mu)$ (nM) | $K_i(\delta)$ (nM) | $IC_{50}$(CYP2D6) (nM) | $IC_{50}$(CYP2C9) (nM) | $IC_{50}$(CYP3A4) (nM) |
|---|---|---|---|---|---|---|---|
| 11 | 10 | 32 | 1900 | 1500 | 1400 | >10000 | >10000 |
| 12 | 3 | 5.8 | 470 | >3000 | 12000 | >10000 | >10000 |
| 13 | 0.86 | 1.4 | 140 | 190 | 9300 | >10000 | >10000 |
| 14 | 1.4 | 1 | 1000 | 510 | >10000 | >10000 | >10000 |
| 15 | 2.7 | 2.8 | 1100 | 470 | >10000 | >10000 | >10000 |
| 16 | 2.1 | 4.1 | 730 | 100 | >10000 | >10000 | >10000 |
| 17 | 0.88 | 1.4 | 1000 | 170 | 7200 | >10000 | 7000 |
| 18 | 5.9 | 9.6 | 880 | 83 | 3400 | 8000 | 4300 |
| 19 | 5.9 | 22 | 1100 | 64 | 6300 | >10000 | 2900 |
| 20 | 1.7 | 14 | 700 | 28 | 4900 | >10000 | >10000 |
| 21 | 1.3 | 1.6 | 480 | 170 | 5300 | >10000 | 5600 |
| 22 | 2.9 | 4.9 | 1100 | 56 | 5800 | >10000 | 4400 |
| 23 | 25 | 52 | 1400 | 320 | 11000 | >10000 | 4300 |
| 24 | 14 | 55 | 200 | 540 | >10000 | >10000 | >10000 |
| 25 | 0.44 | 0.25 | 100 | 180 | 4900 | >10000 | >10000 |
| 26 | 2.9 | 18 | 790 | 110 | 10000 | >10000 | >10000 |
| 27 | 1.8 | 5.7 | 320 | 240 | >10000 | >10000 | >10000 |
| 28 | 6.2 | 79 | >3000 | >3000 | >10000 | >10000 | >10000 |
| 29 | 2.1 | 27 | >3000 | >3000 | >10000 | >10000 | >10000 |

The potencies of the compounds were determined by testing the ability of a range of concentrations of each compound to inhibit the binding of the non-selective opioid antagonist, [$^3$H]diprenorphine, to the cloned human $\mu$, $\kappa$, and $\delta$ opioid receptors, expressed in separate cell lines. All the compounds of the invention that were tested (Examples 11 to 29) bind with high affinity to the human cloned $\kappa$ opioid receptor. These compounds display various range of selectivity $\kappa/\mu$ and $\kappa/\delta$. The potencies of the agonists were assessed by their abilities to stimulated [$^{35}$S]GTP$\gamma$S binding to membranes containing the cloned human $\kappa$ opioid receptors. All the compounds tested were full agonist at $\kappa$ opioid receptor with $EC_{50}$ values in the nanomolar range. None of the compounds tested had any detectable antagonist activity or a stereoisomer, prodrug, pharmaceutically acceptable salt, hydrate, solvate, acid salt hydrate, N-oxide or isomorphic crystalline form thereof;

wherein, independently:

n is an integer from 0 to 4;

$R_1$ is H or —OH;

$R_2$ is an optionally substituted alkyl or optionally substituted aryl;

$R_3$ is H, optionally substituted alkyl, or, when taken together with $R_2$, forms an optionally substituted 4–7 membered heterocycloalkyl ring;

$R_4$ is H or optionally substituted alkyl;

$R_5$ is optionally substituted alkyl, optionally substituted aryl or optionally substituted heteroaryl; and R$_6$ and R$_7$ are H; with the proviso that when n is 0, R$^1$ is hydrogen, R$^3$ is methyl, R$^4$ is hydrogen and R$^5$ is methyl or unsubstituted phenyl, then R$^2$ is other than unsubstituted phenyl, methoxyphenyl, hydroxyphenyl or methanesulfonylaminophenyl, and when n is 0, R$^1$ is hydroxy, R$^3$ is methyl, R$^4$ is hydrogen and R$^5$ is methyl, then R$^2$ is other than unsubstituted phenyl or trifluoromethylphenyl.

2. A compound according to claim 1, wherein n is 1.
3. A compound according to claim 1, wherein R$_1$ is H.
4. A compound according to claim 1, wherein R$_1$ is —OH.
5. A compound according to claim 1, wherein R$_2$ is optionally substituted alkyl.
6. A compound according to claim 5, wherein R$_2$ is isopropyl.
7. A compound according to claim 1, wherein R$_2$ is optionally substituted aryl.
8. A compound according to claim 7, wherein R$_2$ is phenyl.
9. A compound according to claim 1, wherein R$_3$ is H or optionally substituted alkyl.
10. A compound according to claim 9, wherein R$_3$ is methyl.
11. A compound according to claim 1, wherein R$_2$ and R$_3$ form an optionally substituted 4- to 7-membered heterocycloalkyl ring.
12. A compound according to claim 1, wherein R$_4$ is H or lower alkyl.
13. A compound according to claim 12, wherein R$_4$ is H or methyl.
14. A compound according to claim 1, wherein R$_5$ is optionally substituted alkyl.
15. A compound according to claim 1 of Formula II:

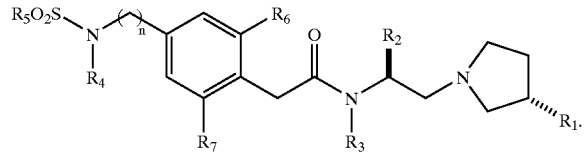

II

16. A compound according to claim 1 of Formula III:

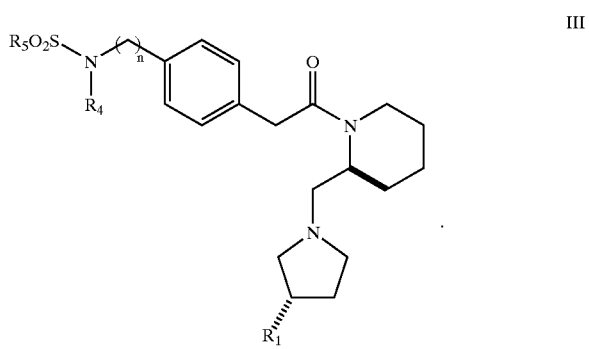

III

17. A compound according to claim 1, wherein said compound is 2-[4-(methanesulfonylamino-methyl)-phenyl]-N-methyl-N-[1-(S)-phenyl-2-pyrrolidin-1-ylethyl]-acetamide.
18. A compound according to claim 1, wherein said compound is N-{2-[3-(S)-hydroxy-pyrrolidin-1-yl]-1-(S)-phenyl-ethyl}-2-[4-(methanesulfonylamino-methyl)-phenyl]-N-methyl-acetamide.
19. A pharmaceutical composition, comprising:
   a pharmaceutically acceptable carrier; and
   an effective amount of a compound according to claim 1.
20. A pharmaceutical composition according to claim 19, further comprising an effective amount of at least one opioid.
21. A pharmaceutical composition according to claim 20, wherein said opioid is selected from the group consisting of alfentanil, buprenorphine, butorphanol, codeine, dezocine, dihydrocodeine, fentanyl, hydrocodone, hydromorphone, levorphanol, meperidine (pethidine), methadone, morphine, nalbuphine, oxycodone, oxymorphone, pentazocine, propiram, propoxyphene, sufentanil, tramadol and mixtures thereof.
22. A pharmaceutical composition according to claim 19, further comprising an effective amount of a compound selected from the group consisting of antibiotics, antivirals, antifungals, anti-inflammatories, anesthetics and mixtures thereof.
23. A compound according to claim 16, wherein said compound is N-[4-(2-{2-[3-(S)-hydroxy-pyrrolidin-1-ylmethyl]-(S)-piperidin-1-yl}-2-oxo-ethyl)benzyl]methanesulfonamide.

* * * * *